United States Patent
Visscher et al.

(10) Patent No.: US 10,386,623 B2
(45) Date of Patent: Aug. 20, 2019

(54) ADAPTER FOR MICROSCOPIC IMAGING

(71) Applicant: Inscopix, Inc., Palo Alto, CA (US)

(72) Inventors: Koen Visscher, Tucson, AZ (US);
Shung Chieh, Sunnyvale, CA (US);
Arash Tajik, Redwood City, CA (US)

(73) Assignee: INSCOPIX, INC., Palo Alto, CA (US)

( * ) Notice: Subject to any disclaimer, the term of this patent is extended or adjusted under 35 U.S.C. 154(b) by 3 days.

(21) Appl. No.: 15/697,702

(22) Filed: Sep. 7, 2017

(65) Prior Publication Data
US 2018/0074306 A1 Mar. 15, 2018

Related U.S. Application Data

(60) Provisional application No. 62/466,946, filed on Mar. 3, 2017, provisional application No. 62/394,016, filed on Sep. 13, 2016.

(51) Int. Cl.
G02B 21/00 (2006.01)
G02B 21/06 (2006.01)
(Continued)

(52) U.S. Cl.
CPC .......... G02B 21/18 (2013.01); A61B 1/00186 (2013.01); A61B 5/0064 (2013.01); A61B 5/0068 (2013.01); A61B 5/0084 (2013.01); G01N 1/44 (2013.01); G02B 21/367 (2013.01); G06T 3/0081 (2013.01); G06T 7/32 (2017.01); G06T 7/33 (2017.01); G06T 7/38 (2017.01); G06T 11/003 (2013.01); H04N 5/23212 (2013.01); A61B 5/0071 (2013.01); G06T 2207/10016 (2013.01);
(Continued)

(58) Field of Classification Search
None
See application file for complete search history.

(56) References Cited

U.S. PATENT DOCUMENTS 4,244,634 A 1/1981 Dianetti et al.
5,349,468 A 9/1994 Rathbone et al.
(Continued)

FOREIGN PATENT DOCUMENTS

WO WO-2015079268 A1 6/2015

OTHER PUBLICATIONS

Packer AM, Peterka DS, Hirtz JJ, Prakash R, Deisseroth K, Yuste R. Two-photon optogenetics of dendritic spines and neural circuits. Nat Methods. 2012;9(12):1202-5)) (Year: 2012).*
(Continued)

*Primary Examiner* — Alison Slater
(74) *Attorney, Agent, or Firm* — Wilson, Sonsini, Goodrich & Rosati

(57) ABSTRACT

Disclosed herein are adapters configured to be optically coupled to a plurality of microscopes, said adapter comprising: a) a first microscope interface configured to optically couple a first microscope to an optical element in optical communication with an optical probe; b) a second microscope interface configured to optically couple a second microscope to the optical element in optical communication with the optical probe; and c) an optical arrangement configured to direct light collected from a sample with aid of the optical probe to (1) the first microscope and second microscope simultaneously, or (2) the first microscope or second microscope selectively.

42 Claims, 7 Drawing Sheets

(51) Int. Cl.

| | |
|---|---|
| *G02B 21/18* | (2006.01) |
| *A61B 5/00* | (2006.01) |
| *G01N 1/44* | (2006.01) |
| *H04N 5/232* | (2006.01) |
| *G06T 11/00* | (2006.01) |
| *G06T 7/38* | (2017.01) |
| *G06T 7/32* | (2017.01) |
| *G06T 3/00* | (2006.01) |
| *G02B 21/36* | (2006.01) |
| *A61B 1/00* | (2006.01) |
| *G06T 7/33* | (2017.01) |

(52) U.S. Cl.
CPC ............ *G06T 2207/10056* (2013.01); *G06T 2207/20024* (2013.01); *G06T 2207/20056* (2013.01)

(56) References Cited

U.S. PATENT DOCUMENTS

| | | | |
|---|---|---|---|
| 6,466,366 B1 | 10/2002 | Dominique | |
| 8,270,071 B2 | 9/2012 | Glaser et al. | |
| 8,346,346 B1 | 1/2013 | Schnitzer et al. | |
| 8,788,021 B1 | 7/2014 | Flusberg et al. | |
| 9,161,694 B2 | 10/2015 | Schnitzer et al. | |
| 9,195,043 B2 | 11/2015 | Ghosh et al. | |
| 9,474,448 B2 | 10/2016 | Ghosh et al. | |
| 9,498,135 B2 | 11/2016 | Ghosh et al. | |
| 9,629,554 B2 | 4/2017 | Ghosh et al. | |
| 9,636,020 B2 | 5/2017 | Flusberg et al. | |
| 9,839,361 B2 | 12/2017 | Schnitzer et al. | |
| 10,200,657 B2 | 2/2019 | Ghosh et al. | |
| 2002/0135871 A1 | 9/2002 | Vodyanoy et al. | |
| 2005/0237605 A1 | 10/2005 | Vodyanoy et al. | |
| 2006/0092503 A1 | 5/2006 | Saunders | |
| 2009/0244545 A1* | 10/2009 | Toida ................... | A61B 5/0066 356/477 |
| 2011/0260720 A1* | 10/2011 | Fischer ................ | G01B 21/08 324/229 |
| 2013/0100271 A1 | 4/2013 | Howes et al. | |
| 2013/0260382 A1 | 10/2013 | Ghosh et al. | |
| 2014/0043462 A1* | 2/2014 | Ghosh ................... | H04N 7/183 348/80 |
| 2014/0321772 A1 | 10/2014 | Piché et al. | |
| 2015/0301029 A1 | 10/2015 | Eggan et al. | |
| 2015/0309295 A1* | 10/2015 | Cocker ................. | G03B 17/02 600/476 |
| 2017/0059841 A1 | 3/2017 | Trulson et al. | |
| 2017/0296060 A1 | 10/2017 | Ghosh et al. | |
| 2018/0217364 A1 | 8/2018 | Cocker et al. | |
| 2018/0220106 A1 | 8/2018 | Ghosh | |
| 2018/0296074 A1 | 10/2018 | Trulson et al. | |
| 2018/0303573 A1 | 10/2018 | Trulson et al. | |

OTHER PUBLICATIONS

Edwards et al. Light-Activated Cre Recombinase as a Tool for the Spatial and Temporal Control of Gene Function in Mammalian Cells. ACS Chem. Biol., 2009, 4 (6), pp. 441-445.

International Search Report and Written Opinion dated Nov. 22, 2017 for International PCT Patent Application No. PCT/US2017/050437.

Maes et al. Multimodality image registration by maximization of mutual information. IEEE Trans Med Imaging. Apr. 1997;16(2):187-98.

Nihongaki et al. Photoactivatable CRISPR-Cas9 for optogenetic genome editing. Nat Biotechnol. Jul. 2015;33(7):755-60.

Polstein et al. A light-inducible CRISPR/Cas9 system for control of endogenous gene activation. Nat Chem Biol. Mar. 2015; 11(3): 198-200.

Sorzano et al. Elastic registration of biological images using vector-spline regularization. IEEE Trans Biomed Eng. Apr. 2005;52(4):652-63.

Yu, et al. Interaction between bevacizumab and murine VEGF-A: a reassessment. Invest Ophthalmol Vis Sci. Feb. 2008;49(2):522-7. doi: 10.1167/iovs.07-1175.

Co-pending U.S. Appl. No. 15/403,819, filed Jan. 11, 2017.
Co-pending U.S. Appl. No. 15/830,894, filed Dec. 4, 2017.
Co-pending U.S. Appl. No. 16/227,044, filed Dec. 20, 2018.

* cited by examiner

ADAPTER FOR MICROSCOPIC IMAGING

CROSS-REFERENCE

This application claims the benefit of priority to U.S. Provisional Patent Application No. 62/394,016, filed Sep. 13, 2016, and U.S. Provisional Patent Application No. 62/466,946, filed Mar. 3, 2017, the entire contents of which are incorporated herein by reference.

BACKGROUND OF THE INVENTION

The disclosed invention relates to microscope systems for in vitro and in vivo imaging, and specifically to an adapter that facilitates alignment of images captured by two or more microscopes used to simultaneously or sequentially image a sample or subject. In some instances, the adapter may be used with microscope systems that can be mounted on live subjects for in vivo imaging of, for example, brain tissue.

SUMMARY OF THE INVENTION

Disclosed herein are adapters configured to be optically coupled to a plurality of microscopes, said adapters comprising: a) a first microscope interface configured to optically couple a first microscope to an optical element in optical communication with an optical probe; b) a second microscope interface configured to optically couple a second microscope to the optical element in optical communication with the optical probe; and c) an optical arrangement configured to direct light collected from a sample with aid of the optical probe to (1) the first microscope and second microscope simultaneously, or (2) the first microscope or second microscope selectively.

In some embodiments, the first microscope is a one-photon microscope. In some embodiments, the second microscope is a two-photon microscope. In some embodiments, the first microscope and the second microscope are of different types. In some embodiments, the first microscope interface is configured to permit the first microscope to contact a housing of the adapter. In some embodiments, the first microscope interface is configured to permit the adapter to bear the weight of the first microscope. In some embodiments, the first microscope weighs 20 grams or less. In some embodiments, the first microscope has a volume of 30 cm$^3$ or less. In some embodiments, the second microscope interface is configured to permit the second microscope to contact a housing of the adapter. In some embodiments, the second microscope interface is configured to permit the second microscope to bear the weight of the adapter. In some embodiments, the first microscope interface and the second microscope interface are provided on a housing. In some embodiments, the first microscope interface and the second microscope interface are provided on different sides of the housing. In some embodiments, at least a portion of the optical probe extends out of the housing. In some embodiments, the optical element is contained within the housing. In some embodiments, the optical probe is attachable and separable from the adapter. In some embodiments, the optical probe comprises a GRIN lens. In some embodiments, the optical element in optical communication with the optical probe is a mirror. In some embodiments, the mirror is configured to rotate about an axis when the optical arrangement is configured to direct the light to the first microscope or second microscope selectively. In some embodiments, the mirror is configured to translate linearly when the optical arrangement is configured to direct light to the first microscope or second microscope. In some embodiments, the optical element is a beamsplitter when the optical arrangement is configured to direct the light to the first microscope and the second microscope simultaneously. In some embodiments, the first microscope and the second microscope are configured to generate images based on the light collected from the sample. In some embodiments, the adapter is configured to cause an image generated by the first microscope and an image generated by the second microscope to align. In some embodiments, the first microscope interface and the second adapter interface allow the adapter to be coupled and decoupled from the first microscope and the second microscope. In some embodiments, the second microscope interface is configured to allow the adapter to be coupled to a plurality of different types of microscopes. In some embodiments, the second microscope interface and the second adapter interface comprise threaded features that mate with each other. In some embodiments, the first microscope interface is configured to be directly connected to an objective lens of the first microscope. In some embodiments, the second microscope interface is configured to be directly connected to an objective lens of the second microscope. In some embodiments, the adapter further comprises a compensator to correct for beam shift and improve a positional accuracy of a stimulation light beam as it impinges on a target region within a field-of-view of the first microscope or the second microscope. In some embodiments, the compensator is a fixed component of the adapter and is oriented at a 45° angle relative to the axis of the stimulation light beam. In some embodiments, the compensator is installed in one position of a multi-position mirror holder which further comprises a dichroic reflector in a different position. In some embodiments, the multi-position mirror holder is a rotary mirror wheel or a linear slider.

Also disclosed herein are adapters configured to be optically coupled to a first microscope and a second microscope, said adapters comprising: a) a first objective lens configured to be optically coupled to the first microscope; b) a second objective lens configured to be optically coupled to an optical probe; and c) an optical arrangement configured to direct light collected from a sample with aid of the optical probe to the first objective lens and an interface configured to optically couple the second microscope (1) simultaneously, or (2) selectively at different times. In some embodiments, the first objective lens is an infinity corrected lens. In some embodiments, the first objective lens and the second objective lens have at least one different optical property. In some embodiments, the first objective lens and the second objective lens have different optical axes. In some embodiments, the first objective lens has a first optical axis and the second objective lens has a second optical axis that is substantially perpendicular to the first optical axis. In some embodiments, the first objective lens is supported by a housing of the adapter. In some embodiments, the second objective lens is supported by a housing of the adapter. In some embodiments, the second objective lens is supported on a different side of the housing than the first objective lens. In some embodiments, the first objective lens has a diameter of about 5 cm or less. In some embodiments, the first objective lens has a numerical aperture of 0.95 or less. In some embodiments, the first objective lens has a working distance of 20 mm or less. In some embodiments, the second objective lens has a diameter of about 5 cm or less. In some embodiments, the second objective lens has a numerical aperture of 0.95 or less. In some embodiments, the second objective lens has a working distance of 20 mm or less. In some embodiments, the optical probe and the second objective lens are in optical alignment. In some embodiments, the optical probe is attachable and separable from the adapter. In some embodiments, the optical probe comprises a GRIN lens. In some embodiments, the optical arrangement comprises an optical element in optical communication with the first objective lens and the interface. In some embodiments, the optical element is a mirror. In some embodiments, the mirror is configured to rotate about an axis when the optical arrangement is configured to direct the light to the first objective lens and the interface selectively at different times. In some embodiments, the optical element is a beamsplitter when the optical arrangement is configured to direct the light to the first objective lens and the interface simultaneously. In some embodiments, the first microscope and the second microscope are configured to generate images based on the light collected from the sample. In some embodiments, the adapter is configured to cause an image generated by the first microscope and an image generated by the second microscope to align. In some embodiments, the adapter further comprises a compensator to correct for beam shift and improve a positional accuracy of a stimulation light beam as it impinges on a target region within a field-of-view of the first microscope or the second microscope. In some embodiments, the compensator is a fixed component of the adapter and is oriented at a 45° angle relative to the axis of the stimulation light beam. In some embodiments, the compensator is installed in one position of a multi-position mirror holder which further comprises a dichroic reflector in a different position. In some embodiments, the multi-position mirror holder is a rotary mirror wheel or a linear slider.

Disclosed herein are adapters configured to be optically coupled to a plurality of microscopes, said adapters comprising: a) a housing having a volume of less than about 2,000 cubic centimeters; b) a plurality of microscope interfaces configured to permit at least a first microscope and a second microscope to be simultaneously in optical communication with an optical element; and c) an optical arrangement comprising the optical element, said optical arrangement at least partially contained within the housing and configured to direct light collected from a sample with aid of an optical probe to the first microscope or the second microscope.

In some embodiments, the first microscope is a one-photon microscope. In some embodiments, the second microscope is a two-photon microscope. In some embodiments, the first microscope and the second microscope are of different types. In some embodiments, the plurality of microscope interfaces is configured to permit the first microscope or the second microscope to contact the housing of the adapter. In some embodiments, at least one of the plurality of microscope interfaces is configured to permit the adapter to bear weight of the first microscope. In some embodiments, at least one of the plurality of microscope interfaces is configured to permit the second microscope to bear weight of the adapter. In some embodiments, the housing comprises a probe interface configured to permit the optical probe to be attachable and separable from the adapter. In some embodiments, at least part of the optical probe extends from the housing. In some embodiments, the optical probe comprises a GRIN lens. In some embodiments, the optical arrangement comprises a mirror at least partially enclosed within the housing. In some embodiments, the first microscope and the second microscope are configured to generate images based on the light collected from the sample. In some embodiments, the adapter is configured to cause an image generated by the first microscope and an image generated by the second microscope to align. In some embodiments, the adapter further comprises a compensator to correct for beam shift and improve a positional accuracy of a stimulation light beam as it impinges on a target region within a field-of-view of the first microscope or the second microscope. In some embodiments, the compensator is a fixed component of the adapter and is oriented at a 45° angle relative to the axis of the stimulation light beam. In some embodiments, the compensator is installed in one position of a multi-position mirror holder which further comprises a dichroic reflector in a different position. In some embodiments, the multi-position mirror holder is a rotary mirror wheel or a linear slider.

Disclosed herein are adapters configured to be optically coupled to a plurality of microscopes, said adapters comprising: a) a housing; b) a plurality of microscope interfaces configured to permit at least a first microscope and a second microscope to be simultaneously in optical communication with an optical element; and c) an optical arrangement comprising the optical element, said optical arrangement at least partially contained within the housing and configured to direct light collected from a sample with aid of an optical probe to the first microscope or the second microscope.

In some embodiments, the housing and the optical arrangement collectively weigh less than about 1 kilogram. In some embodiments, the first microscope is a one-photon microscope. In some embodiments, the second microscope is a two-photon microscope. In some embodiments, the first microscope and the second microscope are of different types. In some embodiments, the plurality of microscope interfaces is configured to permit the first microscope or the second microscope to contact the housing of the adapter. In some embodiments, at least one of the plurality of microscope interfaces is configured to permit the adapter to bear weight of the first microscope. In some embodiments, at least one of the plurality of microscope interfaces is configured to permit the second microscope to bear weight of the adapter. In some embodiments, the housing comprises a probe interface configured to permit the optical probe to be attachable and separable from the adapter. In some embodiments, at least part of the optical probe extends from the housing. In some embodiments, the optical probe comprises a GRIN lens. In some embodiments, the optical arrangement comprises a mirror at least partially enclosed within the housing. In some embodiments, the first microscope and the second microscope are configured to generate images based on the light collected from the sample. In some embodiments, the adapter is configured to cause an image generated by the first microscope and an image generated by the second microscope to align. In some embodiments, the housing, optical elements of the optical arrangement, and the first microscope collectively weigh less than about 1 kilogram. In some embodiments, the adapter further comprises a compensator to correct for beam shift and improve a positional accuracy of a stimulation light beam as it impinges on a target region within a field-of-view of the first microscope or the second microscope. In some embodiments, the compensator is a fixed component of the adapter and is oriented at a 45° angle relative to the axis of the stimulation light beam. In some embodiments, the compensator is installed in one position of a multi-position mirror holder which further comprises a dichroic reflector in a different position. In some embodiments, the multi-position mirror holder is a rotary mirror wheel or a linear slider.

Disclosed herein are adapters configured to be optically coupled to a plurality of microscopes, said adapters comprising: a) a housing; b) a plurality of microscope interfaces configured to permit at least a first microscope and a second microscope to be in optical communication with an optical element; and c) an optical arrangement comprising the optical element, said optical arrangement at least partially contained within the housing and configured to direct light collected from a sample with aid of an optical probe to the first microscope or the second microscope.

In some embodiments, the adapter is configured to support a weight of the first microscope or the second microscope. In some embodiments, the first microscope is a one-photon microscope. In some embodiments, the one-photon microscope is a miniature microscope. In some embodiments, the one-photon microscope comprises a weight equal to or less than 5 gr. In some embodiments, the one-photon microscope comprises a light source and an image sensor. In some embodiments, the second microscope is a two-photon microscope. In some embodiments, the adapter is configured to support the first microscope or the second microscope in its entirety. In some embodiments, the first microscope and the second microscope are of different types. In some embodiments, the plurality of microscope interfaces is configured to permit the first microscope or the second microscope to contact the housing of the adapter. In some embodiments, at least one of the plurality of microscope interfaces is configured to permit the adapter to bear weight of the first microscope. In some embodiments, at least one of the plurality of microscope interfaces is configured to permit the second microscope to bear weight of the adapter. In some embodiments, the housing comprises a probe interface configured to permit the optical probe to be attachable and separable from the adapter. In some embodiments, at least part of the optical probe extends from the housing. In some embodiments, the optical probe comprises a GRIN lens. In some embodiments, the optical arrangement comprises a mirror at least partially enclosed within the housing. In some embodiments, the first microscope and the second microscope are configured to generate images based on the light collected from the sample. In some embodiments, the adapter is configured to cause an image generated by the first microscope and an image generated by the second microscope to align. In some embodiments, the adapter further comprises a compensator to correct for beam shift and improve a positional accuracy of a stimulation light beam as it impinges on a target region within a field-of-view of the first microscope or the second microscope. In some embodiments, the compensator is a fixed component of the adapter and is oriented at a 45° angle relative to the axis of the stimulation light beam. In some embodiments, the compensator is installed in one position of a multi-position mirror holder which further comprises a dichroic reflector in a different position. In some embodiments, the multi-position mirror holder is a rotary mirror wheel or a linear slider.

Disclosed herein are methods for selectively exciting optogenetically-modified neurons in a tissue sample, the method comprising: a) providing the adapter of any one of the previous claims, wherein the first microscope is a one-photon microscope, the second microscope is a two-photon microscope, and the optical probe is in optical communication with the tissue sample; and b) using the two-photon microscope to deliver a train of temporally focused laser pulses to selectively excite individual optogenetically-modified neurons, or sub-cellular compartments thereof.

In some embodiments, the first microscope is a one-photon epifluorescence microscope. In some embodiments, the first microscope is a miniature microscope having a weight of 4 grams or less. In some embodiments, the first microscope is a miniature microscope having a volume of 500 mm$^3$ or less. In some embodiments, the method further comprises the use of real-time bandpass filtering of a series of images captured by the one-photon microscope to facilitate focusing.

Also disclosed herein are methods for performing light-controlled genome editing in a subset of cells within a tissue sample, the methods comprising: a) providing the adapter of any one of the previous claims, wherein the optical probe is in optical communication with the tissue sample, and wherein the first microscope is used to image the tissue sample; and b) using the second microscope to trigger a light-activated CRISPR-based or Cre recombinase-based transcription system for performing light-controlled genome editing in the subset of cells within the tissue sample. In some embodiments, the first microscope is a one-photon epifluorescence microscope. In some embodiments, the first microscope is a miniature microscope having a weight of 4 grams or less. In some embodiments, the first microscope is a miniature microscope having a volume of 500 mm$^3$ or less. In some embodiments, the method further comprises the use of real-time bandpass filtering of a series of images captured by the first microscope to facilitate focusing.

Disclosed herein are methods for enhancing the accuracy of alignment of images captured by a one-photon microscope and a two-photon microscope, the methods comprising: a) providing the adapter of any one of the previous claims, wherein the first microscope is a one-photon microscope, and the second microscope is a two-photon microscope; b) projecting a series of images captured by the one-photon microscope into a single image; c) applying a bandpass filter to the projected image created in step (b) to remove low frequency background and high frequency noise; d) identifying a subset of images selected from a z-stack of two-photon optical image slices that overlap with the focal depth of the one-photon image by: (i) generating a moving projection of two-photon optical image slices, wherein the number of two-photon optical image slices included in the projection is determined by dividing the focal depth of the one-photon image by the thickness of the two-photon optical image slice, and wherein the starting optical image slice for the subset of two-photon optical slices included in the moving projection is incremented by a value of one for each sequential projection; (ii) applying the same bandpass filter as used in step (c) to each of the two-photon projections created in step (d)(i); and (iii) calculating the cross-correlation between the filtered one-photon image of step (c) with each of the filtered two-photon projection images of step (d)(ii) to identify that which is best correlated with the one-photon image; (e) applying an elastic registration algorithm to the filtered one-photon image of step (c) and the filtered two-photon projection image identified in step (d)(iii) to generate a set of coordinate transformations; and (f) applying the coordinate transformation to the filtered one-photon image of step (c) or the filtered two-photon projection image identified in step (d)(iii) to align the images.

In some embodiments, the method further comprises the use of real-time bandpass filtering of a series of images captured by the one-photon microscope to facilitate focusing. In some embodiments, the elastic registration algorithm is a vector-spline regularization algorithm.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1:
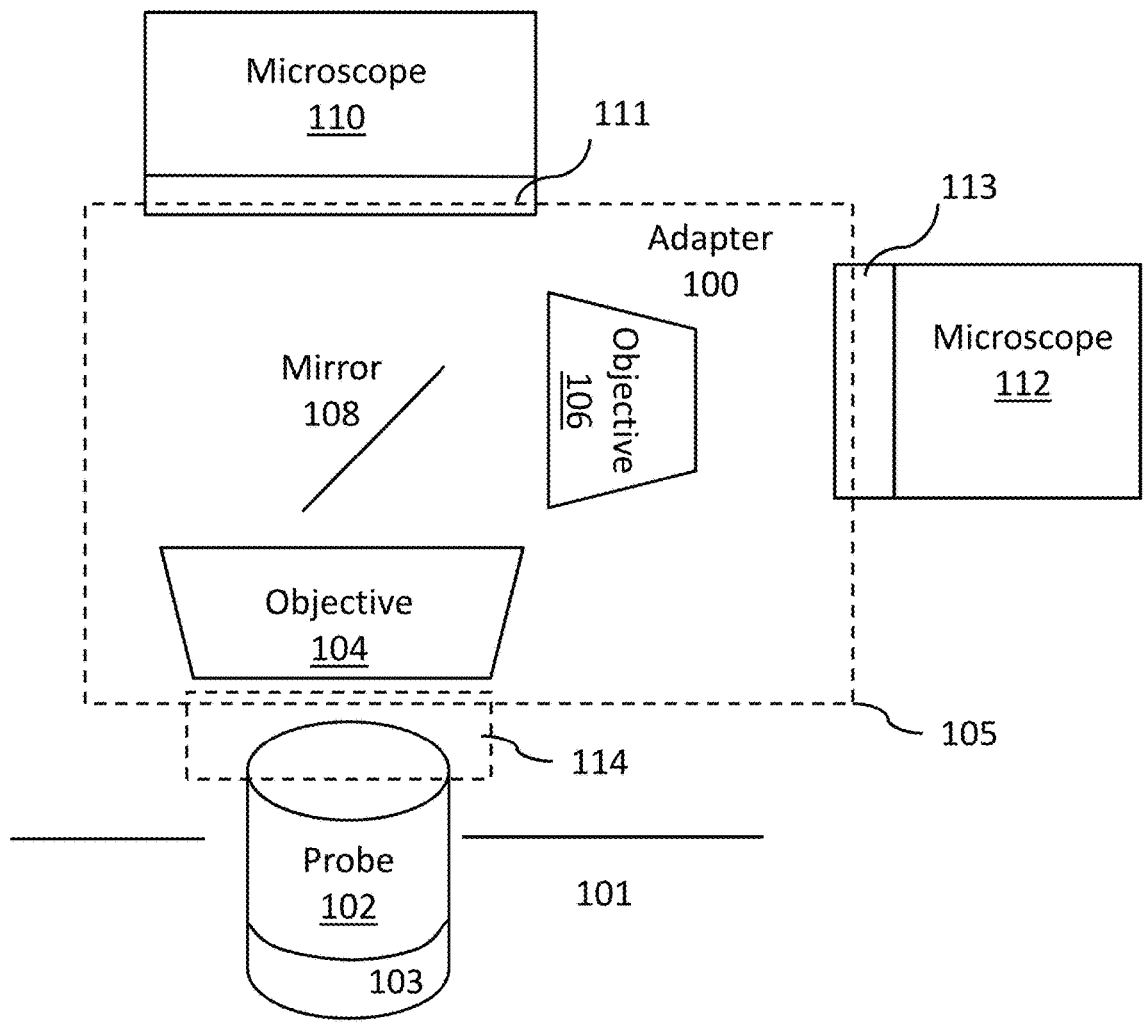
FIG. 1 shows an exemplary schematic diagram of an adapter for use in microscopic imaging, in accordance with embodiments of the invention. The adapter comprises a number of optical elements that may be configured in any of a variety of different optical arrangements.

The invention provides systems, methods, and devices which provide for optical and/or mechanical coupling of microscopes. For example, an adapter may be provided for coupling to microscopes. The microscopes may include various components such as optical components (e.g., objectives, lenses, filters, mirrors, beamsplitters, etc.), wires, physical exteriors such as a housing of the microscope, amongst other things. In some instances, the adapter may be coupled to, or used with, two or more microscopes. Accordingly, the adapter may provide a means for utilizing two or more microscopes in conjunction, simultaneously, in sequence, or selectively as desired. Each of the microscopes described herein may refer to any type of microscope system used for imaging applications. For example, the microscopes may include any type of optical microscope (e.g., bright field, polarizing, phase contrast, differential interference contrast, fluorescence, total internal reflection fluorescence, laser, multiphoton excitation, structured illumination microscopes, etc).

The microscopes referred to herein can be of any size. In some instances, the microscopes may be conventional bench top microscopes. Alternatively, the microscopes may be miniature microscopes. In some instances, the microscopes may be configured or sized to be mechanically as well as optically coupled to a live being. For example, the microscope may be configured to be grounded or, in some instances, mounted on a live being such as mice, rats, birds, and primates, etc. Optionally, the microscope may be mechanically coupled to the live being via other components such as a baseplate. If a microscope is mounted on a live being, the microscope may image the live beings (e.g., in-vivo imaging) while the live beings are freely moving or are still (e.g., while immobilized). In one example, the microscope may image a brain of the live being, while still or freely moving, and may have access to the brain, for example, via gradient-index ("GRIN") lenses. Optionally, the microscope may be coupled to a baseplate that is mounted or affixed to the live being. In some instances, the base plate and/or objective lens (e.g. a GRIN lens) may interface with both a first microscope and a second microscope, e.g. via an adapter. As one example, the adapter may enable different types of microscopes to be used together in conjunction. While the adapter being utilized with two microscopes is primarily discussed herein, it shall be understood that the adapter may enable 3, 4, 5, or more microscopes to be used together.

In some instances, the adapter may comprise one or more interfaces. Each of the interface(s) may allow the adapter to couple to a microscope. For example, the adapter may comprise a first microscope interface and a second microscope interface. Each of the interfaces may allow the adapter to be optically coupled to one or more microscopes. The adapter may in some instances further comprise an optical arrangement configured to direct light (e.g. excitation light) to a sample and/or direct light (e.g. emission light from the sample) to the first microscope and/or second microscope. In some instances, the emitted light may be directed to the first microscope and second microscope simultaneously, sequentially, or selectively as desired. The optical arrangement may include, but are not limited to, any optical elements such as lenses, filters, mirrors, etc. Advantageously, the adapter may allow different types of microscopes to image an identical imaging site. Advantageously, the adapter may enable a miniature microscope to be utilized to image a common imaging site when a live being is freely moving and still (e.g. over a period of time, over different imaging sessions). Advantageously, the adapter may enable a miniature microscope to be utilized to image a common imaging site for a freely moving being that has been, or will be imaged by a multi-photon microscope.

In some instances, the adapter may comprise one or more objective lenses. Each of the objectives may allow the adapter to be optically coupled to another optical device or assembly. For example, in some instances, the adapter may comprise a first objective and a second objective. The first objective may be optically coupled to an optical probe that is partially or fully implanted in the tissue of a subject, thereby facilitating the imaging of tissue within the subject. The second objective may be optically coupled to a microscope system for capturing images using light conveyed by the optical probe. The adapter may thus facilitate detachment and re-attachment of the microscope (optically and/or mechanically) to the implanted optical probe between imaging sessions.

In some instances, the adapter may be a very small and/or light weight device that comprises three or more optical interfaces and an optical arrangement that allows two or more microscopes to be optically and/or mechanically coupled to an optical probe that is partially or fully implanted in the tissue of a subject, thereby facilitating the imaging of tissue within the subject by the two or more microscopes using light conveyed by the optical probe. The adapter may thus facilitate detachment and re-attachment of one or more of the microscope (optically and/or mechanically) to the implanted optical probe between imaging sessions. In some instances, the adapter may be small and/or light weight enough that it is fully or partially supported by one of the two or more microscopes. In some instances, the adapter may be small and/or light weight enough that it is fully or partially supported by one of the two or more microscopes, and may function as the objective of one of the microscopes. In some instances, the adapter may be small and/or light weight enough that it is fully or partially supported by one of the two or more microscopes, and may be used to image a live subject that has been immobilized relative to the position of the one microscope. In some instances, the adapter may be small and/or light weight enough that it is supported by the optical probe, or by a baseplate attached to the subject. In some instances, the adapter may be fully or partially supported by the optical probe, or by a baseplate attached to the subject, and may itself fully or partially support one of the two or more microscopes. In some instances the adapter may be fully or partially supported by the optical probe, or by a baseplate attached to a freely moving subject, and may itself fully or partially support one of the two or more microscopes that is used to image a freely moving subject as it goes about its normal behavior. In some instances, the adapter may be used with a single microscope to image a sample or subject even if it is configured to be optically and/or mechanically coupled to more than one microscope. In these instances, the adapter may function as an objective for the attached microscope, or may function as a means for optically and/or mechanically coupling the microscope to, e.g., an optical probe that has been fully or partially implanted in tissue of a subject.

In some instances, the adapter may comprise three or more optical interfaces and be configured to support the weight of at least one microscope. The adapter may further comprise an optical arrangement that that allows two or more microscopes, including the one supported by the adapter, to be optically and/or mechanically coupled to an optical probe that is partially or fully implanted in the tissue of a subject, thereby facilitating the imaging of tissue within the subject by the two or more microscopes using light conveyed by the optical probe. The adapter may thus facilitate detachment and re-attachment of at least one of the two or more microscopes (optically and/or mechanically) to the implanted optical probe between imaging sessions.

As one example, the adapter may be provided for use with a first microscope and one or more additional microscopes. In some instances, adapter may enable the different microscopes (e.g., one-photon or two-photon microscopes) to perform simultaneous or serial microscopic in vitro or in vivo imaging of a sample or subject (or tissue within a subject). The adapter may enable proper alignment of images captured independently by the first microscope, e.g., a miniature microscope, and the second microscope, e.g., two-photon microscope. In some instances, the adapter may enable proper alignment of images captured by the first microscope and the second microscope without the need for adjustment or displacement of either microscope system or their component optical elements (e.g., without translational or rotational movement). The adapter may enable images captured by the first microscope and the second microscope, e.g., a two-photon microscope, to be fully, substantially, or partially aligned.

The adapter may enable simultaneous images to be captured and/or viewed by the first microscope and the second microscope. Alternatively, the adapter may enable sequential images to be captured and/or viewed by the first microscope and the second microscope. In some instances, the adapter may enable selective viewing (of images captured by the first microscope and the second microscope as a user of the adapter desires). Optionally, the images captured by both microscope systems may be formed by light transmitted via a single optical probe which is in contact with, or partially implanted in, the sample or subject (or tissue within the subject). Various aspects of the invention described herein may be applied to any of the particular applications set forth below or for any other types of imaging applications. It shall be understood that different aspects of the invention can be appreciated individually, collectively, or in combination with each other.

Figure 2:
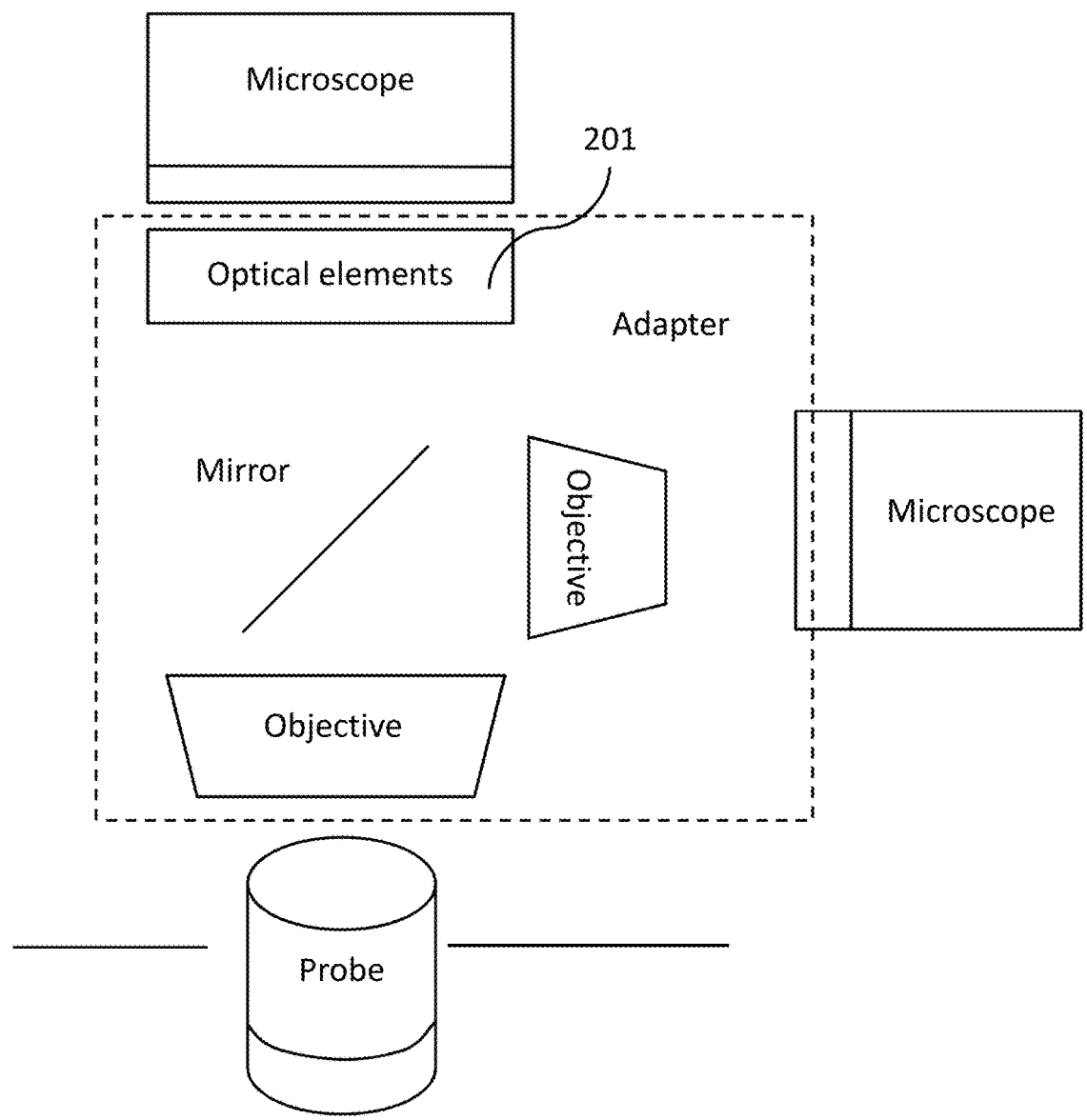
FIG. 2 shows an exemplary schematic diagram of an adapter for use in microscopic imaging, wherein the adapter comprises additional optical components in accordance with embodiments of the invention.

FIGS. 1 and 2 show exemplary schematic diagrams of an adapter, 100 or 200, in accordance with embodiments of the invention. Referring to FIG. 1, the adapter may comprise at least a first objective 104 and mirror 108 that are arranged to direct light between microscope 110 and/or microscope 112. In some instances, the adapter may be used together with an optical probe 102 which is in optical communication with the first objective lens 104 of the adapter. In some instances, optical probe 102 and objective 104 are in optical alignment, i.e., their optical axes are aligned. The probe 102 may be supported on a subject 101 which may comprise a target area to be imaged 203.

The subject may be a human subject or an animal subject. In some embodiments, animal subjects may include rodents (e.g., mice, rats, rabbits, guinea pigs, gerbils, hamsters), simians (e.g., monkeys, chimpanzees, orangutans, gorillas, and humans), equines (e.g. horses), bovines (e.g., cows), canines (e.g., domestic dogs), felines (e.g., domestic cats), avines, insects, or any other types of animals. In some instances, the subjects may weigh less than about 100 kg, 50 kg, 40 kg, 30 kg, 20 kg, 15 kg, 10 kg, 5 kg, 3 kg, 2 kg, 1 kg, 750 grams, 500 grams, 400 grams, 300 grams, 200 grams, 100 grams, 75 grams, 50 grams, 40 grams, 30 grams, 25 grams, 20 grams, 15 grams, 10 grams, 5 grams, 3 grams, or 1 gram. In some embodiments, the probe can be mounted on and/or inserted into a living organism or a non-living organism. The target area may include neural tissue of the subject, but may alternatively or in addition include any target area of the subject, e.g. muscle tissue, skin tissue, etc.

The first objective lens 104 may be configured to be in optical communication with mirror 108. The mirror 108 may be in optical communication with a second objective lens 106, with microscope 112 (e.g., a miniature microscope), and/or with microscope 110 (e.g., a two-photon microscope). An objective lens as used throughout may refer to a lens at or near a surface of a device such as the adapter. The second objective lens 106 may, in some instances, belong to microscope 112, or in some instances may be a component of adapter 100 that is in optical communication with microscope 112. In some instances, the optical axes of objective 104 and objective 106 are different. In some instances, the optical axis of objective 104 and optical axis of objective 106 may be substantially perpendicular to each other, as indicated in FIG. 1. The adapter may further comprise various additional optical elements (e.g., optical elements 201 as illustrated schematically in FIG. 2). The optical elements (or optical components) may include, but are not limited to, lenses or lens systems, optical filters, prisms, beamsplitters, dichroic reflectors, mirrors, optical fibers, diffractive optical elements for correction of chromatic aberration, etc., and may be configured in any of a number of optical arrangements known to those of skill in the art.

The adapter may optionally further comprise one or more interfaces 111, 113, 114 that allow one or more microscopes 110, 112, one or more objectives 106, and/or one or more optical probes 102 to be brought into optical communication with the adapter in a repeatable manner. For instance, the microscope interfaces and/or objective interfaces may allow the microscopes and/or objectives to be repeatedly coupled to the adapter and aligned relative to optical probe 102 in the same manner over multiple uses (i.e., over repeated cycles of attachment and removal). The repeatability of the alignment may allow the adapter and/or microscopes to be easily swapped in and out. The microscopes and/or objectives may easily be aligned to permit high quality, simultaneous or serial imaging by two or more microscopes. In some instances, microscope interfaces 111 and 113 may be configured to be directly connected to an objective lens of a microscope. In some instances, the one or more microscopes coupled to the adapter by means of interfaces 111, 113, etc., may be the same type of microscope. In some instances, the one or more microscopes coupled to the adapter by means of interfaces 111, 113, etc., may be two or more different types of microscope, e.g., microscopes that have different imaging properties such as different fields-of-view, different image resolutions, different depths-of-field, or operating in different wavelength ranges.

An optical probe 102 may be configured to be in optical communication with a target to be imaged (e.g., a structure or tissue within a sample or subject) in such a way that light is transmitted to the target and/or collected from the target via the probe. The optical probe may be an endoscopic probe that may be partially or fully inserted into a subject (or tissue within a subject), or may image an exterior portion of a sample or subject. In some instances, the subject may be a live being, such as a mouse, rat, bird, primate, human, insect, fish, etc. The probe may be coupled to the live beings (e.g., for in vivo imaging) while the live beings are freely moving, freely behaving, or are still. In some instances, the subject may be immobilized or a portion of the subject (e.g., the head) may be immobilized during imaging. The live being may be conscious or may be unconscious. In some embodiments, the live being may or may not be anesthetized. For example, the optical probe may provide optical access to a brain of the live being. The target to be imaged may be a tissue of the live being, such as brain tissue of the live being.

In some instances, the optical probe 102 may be or may include a gradient index (GRIN) lens and/or other relay lens. The GRIN lens can be a lens in which the refractive index of the lens varies along a dimension perpendicular to the optical axis. The gradient index lens may have a pitch of at least about ½, 2/2, 3/2, 4/2, 5/2, 6/2, 7/2, 8/2, 9/2, 10/2, 11/2, 12/2, or 13/2. The gradient index lens may have diameters ranging from 0.001 mm to 5 mm. The gradient index lens may have a numerical aperture (NA) of at least about 0.001, 0.01, 0.1, 0.2, 0.3, 0.4, 0.5, 0.6, 0.7, 0.8, or 0.85. The GRIN lens may comprise one or more flat surfaces. The GRIN lens may have an angled surface. The angle may be a 45 degree angle. In some instances, optical probe may comprise two or more GRIN lenses. In some instances, optical probe 102 may further comprise a right angle prism and corrective optical element in addition to the GRIN lens to correct for aberration due to field curvature when viewing through a cylindrical side of the probe. In some instances, a corrective optical element may be included in the adapter when the probe comprises a right angle prism in addition to the GRIN lens. In some instances, the GRIN probe may comprise a combination of optical corrective elements and GRIN elements, e.g., in color corrected probes, where the corrective elements are sandwiched between multiple GRIN lenses and form a stack of optical elements. In some instances, the optical probe 102 may optionally comprise or be used in conjunction with a cannula (e.g., a metal or glass cannula) at least partially implanted within the subject and within which the GRIN lens is fitted. In these embodiments, the adapter housing may comprise a mechanical coupler to attach the cannula to the adapter. In these embodiments, the mechanical coupler may also align the optical axis of the microscope and that of the GRIN lens probe. In some instances, the optical probe, e.g., a GRIN optical probe, may be a cylindrical probe with a small diameter. The probe (with or without a cannula) may have a diameter of less than or equal to about 10 mm, 5 mm, 4 mm, 3 mm, 2 mm, 1 mm, 0.5 mm, 0.1 mm, 0.05 mm, 0.01 mm, 0.005 mm, or 0.001 mm. The small diameter of the probe may reduce the amount of damage induced upon insertion into the subject. The optical probe may have a length of less than or equal to about 10 mm, 9 mm, 8 mm, 7 mm, 6 mm, 5 mm, 4 mm, 3 mm, 2 mm, or 1 mm.

In some instance, the probe 102 may optionally be supported on the subject with the aid of a mounting structure, such as a base plate. The mounting structure may keep the optical probe relatively stationary relative to the subject. The mounting structure may be provided on an exterior of the subject, such as the head of the subject. The mounting structure and/or the probe may be adhered to the subject (e.g., using adhesives or surgical fasteners). The mounting structure may have a size or shape adapted to fit a living being, for example, so that it may be carried on the head of a mouse or other rodent.

The adapter 100 may be optically coupled to the optical probe 102. The coupling may or may not involve physical coupling. An optical axis of objective lens 104 may line up with an optical axis of probe 102. In some instances, the adapter may not be physically coupled to the probe. For example, the adapter may act as an objective lens of microscope 110 or 112. The probe 102 may move along with the subject 101 (or a stage on which the subject is held). In some instances, the adapter may be located a distance equal to or less than about 30 cm, 25 cm, 20 cm, 15 cm, 10 cm, 5 cm, 1 cm, 0.5 cm, 0.1 cm, 750 um, 500 um, 250 um, 100 um or 50 um to image the target region. In some instances, an objective of the adapter (e.g. objective 104) may be located a distance equal to or less than about 30 cm, 25 cm, 20 cm, 15 cm, 10 cm, 5 cm, 1 cm, 0.5 cm, 0.1 cm, 750 um, 500 um, 250 um, 100 um or 50 um to image the target region.

In some instances, the adapter 100 may be mechanically and/or optically coupled to optical probe 102 by means of probe interface 114 such that the components therein, e.g., objective lens 104, are in optical communication with probe 102. An optical axis of objective lens 104 may line up with an optical axis of probe 102. In some instances, the adapter may have a fixed position relative to the probe. In some instances the mechanical coupling of probe interface 114 may be undone such that adapter 100 is separable and removable from probe 102 after first having been attached. In some instances, the mechanical coupling of probe interface 114 may be permanent such that adapter 100 is not removable from probe 102. Examples of suitable configurations for probe interface 114 include, but are not limited to, mated features on adapter 100 and probe 102 that form a tight press fit, mated threaded features, mated quick-release fittings, mated features that are held in place using set screws, mated features on adapter 100 and probe 102 that are permanently bonded using an adhesive, etc. In some instances, the adapter may be mounted onto the subject. The adapter may or may not be mounted on the probe and/or a mounting structure for the probe. The adapter may be mounted in a manner that allows for repeated alignment between the probe and the first objective when the adapter is removed and/or re-attached.

The optical probe 102 may be in optical communication with an objective lens 104. The objective lens may have any desired optical property. The optical axis of the probe may be aligned with an optical axis of the objective lens. Light reflected, scattered, or emitted from a target area to be imaged may pass through the probe to the objective lens. In some instances, the light may pass through objective lens 104 to a mirror 108. A first objective lens 104 may optionally be configured to provide an infinite focal length (e.g., may have infinity correction). This may be beneficial for use of the adapter with the microscopes, e.g., a two-photon microscope 110. This may allow for a two-photon microscope to be easily coupled to the subject and capture images of the target area via optical probe 102.

In some instances, objective lens 104 (and/or objective 106) may be a single lens. In some instances, objective lens 104 (and/or objective 106) may be compound lenses. In some instances, objective lens 104 (and/or objective 106) may be GRIN lenses. In some instances, objective lens 104 (and/or objective 106) may have a diameter of less than or equal to about 50 mm, 40 mm, 30 mm, 20 mm, 10 mm, 5 mm, 4 mm, 3 mm, 2 mm, 1 mm, 0.5 mm, 0.1 mm, 0.05 mm, 0.01 mm, 0.005 mm, or 0.001 mm. In some instances, objective lens 104 (and/or objective 106) may have a focal length of about 200 mm, about 100 mm, about 50 mm, about 25 mm, about 10 mm, about 5 mm, or about 1 mm. In some instances, objective lens 104 (and/or objective 106) may have a numerical aperture of about 0.95, about 0.85, about 0.75, about 0.65, about 0.55, about 0.45, about 0.40, about 0.25, about 0.1, or about 0.01. In some instances, the NA of the objectives matches the NA of the GRIN probe, e.g., with NA values ranging from about 0.45 to 0.5, which may facilitate optimal light collection. In some instances, objective lens 104 (and/or objective 106) may have a working distance of about 15 μm, 25 μm, 50 μm, 100 μm, 0.2 mm, 0.4 mm, 0.8 mm, 1 mm, 2 mm, 4 mm, 6 mm, 8 mm, 10 mm, 12 mm, 14 mm, 16 mm, 18 mm, or 20 mm. In some instances, objective lens 104 (and/or objective 106) may be corrected for chromatic and/or spherical aberration.

The first objective lens 104 and a second objective lens 106 may optionally be the same type of objective and/or may have one or more of the same mechanical and/or optical properties. The first and second objectives may be the same type of lens or different types of lenses. The first objective and second objective may permit the transmission of near-UV light, visible light, and/or near infrared light. The first objective and/or second objective may focus, collimate, and/or disperse light in a desired fashion. In some embodiments, the first objective and/or second objective may be compatible with infrared and/or fluorescence imaging.

The adapter 100 may also include a mirror 108. In some embodiments, a mirror may be configured to be fully reflective. Light that reaches the mirror may be reflected to another location. For example, light from a first objective 104 may be reflected or directed to a second objective 106. In another example, light from the first objective may be reflected to microscope 110, e.g., a two-photon microscope. When the mirror is fully reflective (e.g., 100% reflective), or mostly reflective (e.g., 50% or more, 75% or more, 90% or more, 95% or more, or 99% or more reflective), the mirror may be movable to direct the reflected light to a desired location. In some instances, mirror 108 may provide a 50/50 split of light directed to microscope 110 and microscope 112. The mirror may move with aid of an actuator (e.g., a motor). Alternatively, the mirror may move with aid of manual manipulation. The mirror may rotate about an axis to direct the light to the second objective or to microscope 110, e.g., the two-photon microscope, selectively. In some instances, the mirror may flip around to change orientations. In some instances, the mirror may slide in-and-out of the optical path to direct light to a different objective or microscope. Thus, the second objective and microscope 110 may receive light from optical probe 102 in an alternative or sequential fashion.

In another example, the mirror 108 may not be fully reflective. The mirror may allow light from the first objective 104 to be split and sent to both the second objective 106 (which may be in optical communication with microscope 112) and microscope 110 simultaneously. The mirror may be a beamsplitter. The mirror may be a dichroic reflector. The mirror may have a coating that may enable the light to be split. Thus, the second objective 106 and microscope 110 may receive light from the probe in a parallel, or simultaneous, fashion.

The mirror may be configured to optically direct light (e.g., excitation light) from a plurality of different types of microscopes such as epifluorescence and multiphoton microscopes, and to direct light (e.g. emitted light from the target area) to a plurality of different types of microscopes. The mirror may be configured to optically direct light (e.g. excitation light) from a plurality of different types of microscopes such as epifluorescence and multiphoton microscopes, and to direct light (e.g. emitted light from the target area) to a plurality of different types of microscopes within a single imaging session. A single imaging session may comprise the collection of one or more images over a continuous period of time. The imaging session may have a duration of less than 1 minute, less than 5 minutes, less than 10 minutes, less than 30 minutes, less than 1 hour, less than 2 hours, less than 5 hours, less than 10 hours, less than 1 day, less than 2 days, less than 5 days, less than 10 days, or less than 30 days. The imaging session may have a duration in a range defined by any two of the preceding values. An imaging session may be defined by a length of time during which a microscope is collecting data. An imaging session may begin when a microscope starts generating images and may end when the microscope stops generating images. An imaging session may begin when microscopes coupled to the adapter starts generating images and may end when the microscopes stop generating images. An imaging session may begin when the microscopes are turned on and may end when the microscopes are turned off. A probe position may or may not be altered during an imaging session. The imaging session may be defined by a length of time while a probe is inserted into the object. The imaging session may start when insertion of the probe into the object begins, and may end when the probe is removed from the object. The position of the probe may be altered during the imaging session. A single imaging session or multiple imaging sessions may occur during a longitudinal study.

In some instances, mirror 108 may be a dichroic reflector configured to discriminate between light within a wavelength range of about 400 nm to 500 nm and light within a wavelength range of about 500 nm and 800 nm. In some instances, mirror 108 may be a dichroic reflector configured to discriminate between light within a wavelength range of about 500 nm to 650 nm and light within a wavelength range of about 350 nm and 560 nm. In some instances, mirror 108 may be a dichroic reflector configured to pass infrared (IR)

light from a two-photon microscope and reflect all of the excitation light provided by a miniature one-photon fluorescence microscope.

The adapter may include a housing 105, as indicated by the dashed lines in FIGS. 1 and 2. The housing may partially or completely enclose one or more components of the adapter within the housing, e.g., the housing may enclose the mirror. In some instances, the housing may be light-tight or substantially light-tight. The first objective may be provided within the housing, may be integrated directly with the housing, or may be mounted on the housing. In some instances, the housing may have a volume of less than about 2,000 cubic centimeters, 1,500 cubic centimeters, 1,000 cubic centimeters, 500 cubic centimeters, 250 cubic centimeters, 100 cubic centimeters, 50 cubic centimeters, 25 cubic centimeters, 20 cubic centimeters, 15 cubic centimeters, 12 cubic centimeters, 10 cubic centimeters, 8 cubic centimeters, 7 cubic centimeters, 6 cubic centimeters, 5 cubic centimeters, 4 cubic centimeters, 3 cubic centimeters, 2 cubic centimeters, 1 cubic centimeter, 0.5 cubic centimeters, or 0.1 cubic centimeters. In some instances, the adapter housing may have a long dimension that is less than about 50 cm, 40 cm, 30 cm, 20 cm, 10 cm, 5 cm, 4.5 cm, 4 cm, 3.5 cm, 3 cm, 2.5 cm, 2 cm, 1.5 cm, 1 cm, or 0.5 cm. In some instances, the collective weight of the adapter housing and the optical elements of the optical arrangement contained therein may be equal or less than about 1 kg, 0.9 kg, 0.8 kg, 0.7 kg, 0.6 kg, 0.5 kg, 0.4 kg, 0.3 kg, 0.2 kg, 0.1 kg, 90 grams, 80 grams, 70 grams, 60 grams, 50 grams, 40 grams, 30 grams, 20 grams, 10 grams, 9 grams, 8 grams, 7 grams, 6 grams, 5 grams, 4 grams, 3 grams, 2 grams, or 1 gram. In some instances, the ratio of the longest adapter housing dimension to that of one of the microscopes attached to the adapter may be at most 1:1, 1:10, 1:100, or 1:1000.

In some instances, interfaces 111, 113, and 114 may be provided within the housing, may be integrated directly with the housing, or may be mounted on the housing. In some instances, at least a first microscope interface is configured to permit at least a first microscope to contact the housing of the adapter. In some instances, at least a first microscope interface is configured to permit the adapter to bear the weight of at least a first microscope. In some instances, a first and a second microscope interface may be provided on the same side of the housing. In some instances, a first and a second microscope interface may be provided on different sides of the housing. In some instances, a first and a second microscope interface may be provided such that the adapter is configured to orient a first and a second microscope at 90 degrees relative to each other. In some instances, the adapter may be configured such that the first and second microscopes are positioned at about 180 degrees, 170 degrees, 160 degrees, 150 degrees, 140 degrees, 130 degrees, 120 degrees, 110 degrees, 100 degrees, 90 degrees, 80 degrees, 70 degrees, 60 degrees, 50 degrees, 40 degrees, 30 degrees, 20 degrees, or 10 degrees relative to each other. In some instances, the adapter may be configured such that the position of the first and second microscopes relative to each other is adjustable. Examples of suitable configurations for microscope and/or objective interfaces 111 and 113 include, but are not limited to, mated features on adapter 100 and microscopes 110 or 112 that form a tight press fit, mated threaded fittings, mated quick-release fittings, etc. In some instances, at least a portion of optical probe 102 extends out of the housing. In some instances, mirror 108 is at least partially enclosed within the housing.

In some instances, the adapter may include the second objective 106. Alternatively, the second objective may be separate from the adapter, e.g., may be part of microscope 112, but may be in optical communication with the adapter. The second objective may be within or formed on a housing 105.

The adapter may be configured to be attached to, or optically coupled with, various commercially-available microscopes. For example, the adapter may be configured to be coupled to miniature, one-photon epifluorescence microscopes or to two-photon microscopes. Optionally, the adapter may be configured to be partially or fully coupled with an objective of a microscope, e.g., a two-photon microscope. Optionally, the adapter may be configured to function as an objective of a microscope, e.g., two-photon microscope. It is to be understood that the adapters of FIGS. 1 and 2 may further comprise various optical elements that are not shown, or may comprise the optical probe 102 and/or the microscope 112. In some instances, the adapter may comprise a focusing mechanism. In some instances, the adapter may not comprise a focusing mechanism. Additionally, while the adapters of FIGS. 1 and 2 are illustrated to include certain elements (e.g., objective 106), it is to be understood that the adapter may exclude some of the optical elements shown. For example, the adapter may not comprise objective 106, and objective 106 may be a part of microscope 112.

The adapter may be in optical communication with a microscope 112. In some instances, the adapter may be mechanically and/or optically coupled to microscope 112 via microscope interface 113. In some instances, the adapter may attach to the microscope in a manner that an objective would be attached. Alternatively, the microscope may be mounted onto a housing of the adapter and may form a part of the adapter. The microscope may or may not be separable from the housing of the adapter. The second objective 106, if present, may be a part of, or in optical communication with microscope 112. Alternatively, the adapter need not contact microscope 112. The mirror within the adapter may permit optical communication between the first objective 104 and the microscope. The second objective 106 may function as an objective of microscope 112. The second objective may be a part of the microscope and may or may not be separable from the adapter. Alternatively, the second objective may be separate from the microscope. The adapter may function as an objective lens system for the microscope 112. Adapters with different mechanical and/or optical properties (e.g., having different objective lens focal lengths, numerical apertures, and/or mirror reflectance properties) may be attached and detached to microscope 112 (or to microscope 110). Different adapters may be swapped for one another.

The microscope 112 may be any type of microscope. In some instances, the microscope 112 may be a one-photon, epifluorescence microscope. The microscope may be a miniature microscope or a benchtop microscope. In some examples, the microscope may be of any size suitable for coupling to a live being. In some instances, the microscope may be of a size and/or weight that can be mounted on and carried by the live being. For example, the microscope may be attached to the living being through appropriate means (e.g., using a baseplate, and/or adapter) and may be carried while the live being goes about its activities. In some instances, the microscope may be equal or less than about 30 grams, 25 grams, 20 grams, 15 grams, 10 grams, 9 grams, 8 grams, 7 grams, 6 grams, 5 grams, 4 grams, 3 grams, 2 grams, or 1 gram in weight. In some instances, the collective weight of the adapter housing, the optical elements of the optical arrangement contained therein, and the microscope may be equal or less than about 1 kg, 0.9 kg, 0.8 kg, 0.7 kg, 0.6 kg, 0.5 kg, 0.4 kg, 0.3 kg, 0.2 kg, 0.1 kg, 100 grams, 90 grams, 80 grams, 70 grams, 60 grams, 50 grams, 40 grams, 30 grams, 20 grams, 10 grams, 9 grams, 8 grams, 7 grams, 6 grams, 5 grams, 4 grams, 3 grams, 2 grams, or 1 gram. In some instances, the microscope may comprise a maximum dimension equal to or less than about 5 inches, 4 inches, 3 inches, 2 inches, or 1 inch. Optionally, the microscope may comprise a volume equal or less than about 100 cubic inches, 75 cubic inches, 50 cubic inches, 30 cubic inches, 20 cubic inches, 10 cubic inches, 5 cubic inches, 3 cubic inches, 2 cubic inches, 1 cubic inch, 0.75 cubic inches, or 0.5 cubic inches. In some instances, the microscope may comprise a volume equal or less than about 2,000 $cm^3$, 1,500 $cm^3$, 1,000 $cm^3$, 500 $cm^3$, 100 $cm^3$, 50 $cm^3$, 40 $cm^3$, 30 $cm^3$, 20 $cm^3$, 10 $cm^3$, 1,000 $mm^3$, 800 $mm^3$, 600 $mm^3$, 400 $mm^3$, 200 $mm^3$, 100 $mm^3$, or 50 $mm^3$. The microscope may comprise various optical elements, e.g. lenses, electronic lenses (e.g., e-lenses, deformable lenses, or tunable lenses), bandpass filters, long-pass filters, short-pass filters, dichroic reflectors, mirrors, beamsplitters, prisms, etc. The microscope may comprise one or more image sensor arrays such as CCD or CMOS image sensors. Optionally, the microscope may comprise one or more light sources, e.g. LEDs, SLEDs, diode lasers, or fiber-coupled lasers.

Microscope 112 may be capable of performing high resolution imaging, e.g., bright-field, dark-field, or fluorescence imaging, across a specified field of view. For example, the microscope may be capable of performing cellular or subcellular resolution imaging. In some instances, microscope 112 (and/or microscope 110) may be capable of imaging with a resolution of at least 0.1 um, 0.5 um, 1 um, 1.5 um, 2 um, 2.5 um, 3 um, 4 um, 5 um, 10 um, 20 um, 50 um, or 100 um at the center of the field of view. In some instances, microscope 112 (and/or microscope 110) may be capable of imaging with a resolution of at least 0.1 um, 0.5 um, 1 um, 1.5 um, 2 um, 2.5 um, 3 um, 4 um, 5 um, 10 um, 20 um, 50 um, or 100 um across the field of view. In some instances, the field of view for microscope 112 (and/or microscope 110) may be at least about 0.01 $mm^2$, 0.05 $mm^2$, 0.1 $mm^2$, 0.2 $mm^2$, 0.3 $mm^2$, 0.4 $mm^2$, 0.5 $mm^2$, 1 $mm^2$, 5 $mm^2$, 10 $mm^2$, 20 $mm^2$, 30 $mm^2$, 40 $mm^2$, 50 $mm^2$, 60 $mm^2$, 70 $mm^2$, 80 $mm^2$, 90 $mm^2$, or 100 $mm^2$. As previously described, a sensor array may be used to image the target region of the sample or subject. In some instances, microscope 112 may be configured to perform multicolor fluorescence imaging. Such microscopes may comprise: (i) one or more light sources that provide excitation light at one or more wavelengths (or wavelength ranges), (ii) a first optical arrangement configured to deliver excitation light at the one or more excitation wavelengths (or wavelength ranges) to the sample or subject, (iii) a second optical arrangement configured to collect emitted fluorescent light at one or more wavelengths (or wavelength ranges) from the sample or subject and form one or more images therefrom, and (iv) one or more image sensors to capture the one or more images. The first and second optical arrangements may comprise a variety of optical components, including but not limited to, objective lenses, lenses, filters, mirrors, prisms, beamsplitters, dichroic reflectors, and the like.

Figure 3:
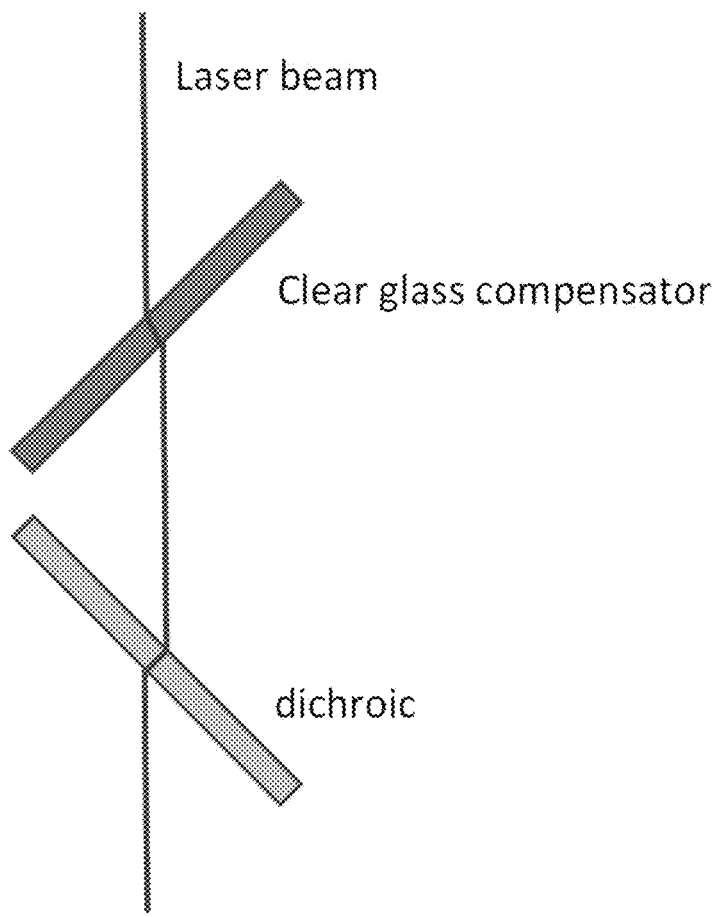
FIG. 3 provides a schematic illustration of the use of a compensator to correct for the beam displacement caused by passing a laser beam through a dichroic reflector, thereby improving the positioning accuracy of the laser beam when it impinges on a target region, e.g., a single cell, within the field-of-view of an imaging system of the present disclosure.

In some instances, microscope 112 may be a microscope designed for use in performing optogenetic studies. Such microscope systems may comprise: (i) an imaging light directing arrangement of optical elements that directs imaging light from an imaging light source to a sample in a field-of-view of the microscope system, (ii) a stimulation light directing arrangement of optical elements that directs stimulation light from a stimulation light source to at least a portion of the sample for optogenetic stimulation of that portion of the sample while the sample is illuminated by the imaging light, (iii) an optical path that directs the imaging light and the stimulation light to the sample, wherein the imaging light and the stimulation light are transmitted through one or more shared optical elements in the optical path, and wherein the area of the sample receiving the stimulation light overlaps with that receiving the imaging light, and (iv) an image sensor that receives light emitted from the sample to generate an image of the sample while the stimulation light is directed to a portion of the sample. In some instances, such microscope systems designed for use in performing optogenetic studies may further comprise a compensator such as that illustrated in FIG. 3 to improve the positional accuracy of the stimulation light (e.g., a stimulation laser beam or collimated stimulation light produced by the stimulating light directing arrangement) as it impinges on a target region, e.g., a single cell or a selected group of cells, within the field-of-view of the microscope system. As indicated in FIG. 3, when, e.g., a laser beam passes through a dichroic reflector of the adapter, the beam may be displaced. This may result in a shift in the position of the beam relative to the sample within the field-of-view of the microscope system, and thus a loss of positional accuracy may occur when stimulating, e.g., single cells. To correct for this beam shift, a compensator may be used. In some instances, the compensator may comprise a clear glass plate (e.g., a clear glass compensator). In some instances, the compensator may be oriented at an angle of 45° relative to the axis of the stimulating laser beam (i.e., perpendicular to the dichroic reflector when both are oriented at an absolute angle of 45° relative to the optical axis). In some instances, the angle may be equal to about 15°, 30°, 45°, 60°, 75°, or any value there between, and the dichroic reflector may be oriented at an angle having the corresponding negative value. The compensator may be optically transparent at the wavelengths used for stimulation. In some instances, the compensator may have the same thickness as the dichroic reflector so as to accurately compensate for the beam shift. Alternatively or in addition, the compensator may be constructed of the same material (e.g., an optical glass) or a material having the same index of refraction as the dichroic reflector so as to accurately compensate for the beam shift. In some instances, the compensator may have a different thickness and/or may be constructed of a different material than the dichroic reflector, and the compensator and dichroic reflector may be oriented at different absolute angles relative to the optical axis. In some instances, the compensator may be a fixed component of the adapter. In some instances, the adapter may comprise more than one compensator, e.g., the adapter may comprise two or more compensators to correct for beam shift of two or more laser beams or collimated stimulation light beams.

Another approach to the issue of correcting for beam shift may be to use a multi-position mirror holder (or multi-position filter holder) with the dichroic reflector and the compensator installed in two separate positions, e.g., a first position and a second position respectively. To calibrate the beam position using the adapter, one can position the compensator in the light path (e.g., position 2 on the multi-position mirror holder) and follow the beam calibration procedure on the multiphoton system. Then, one can switch to the dichroic mirror position (e.g., position 1 on the multi-position mirror holder) and follow up with photostimulation and imaging experiments using the adapter. The multi-position mirror holder may have any of a variety of configurations known to those of skill in the art, e.g., a rotary mirror (or filter) wheel, a linear slider, etc.

The adapter may be in optical communication with a microscope 110. In some instances, the adapter may be mechanically and/or optically coupled to microscope 110 via microscope interface 111. In some instances, the adapter may attach to microscope 110 in a manner that an objective would be attached. In some instances, the adapter may be optically coupled to microscope 110 via an optical fiber or liquid light guide. Alternatively, the adapter need not contact microscope 110. The mirror within the adapter may permit optical communication between the first objective 104 and the microscope. The adapter may function as an objective lens system for the microscope 110. Adapters with different mechanical and/or optical properties (e.g., having different objective lens focal lengths, numerical apertures, and/or mirror reflectance properties) may be attached and detached to microscope 110. Different adapters may be swapped for one another.

The microscope 110 may be any type of microscope, e.g., a wide-field epifluorescence microscope, multiphoton microscope, confocal laser scanning microscope, coherent Raman scattering microscope, etc. In some instances, the microscope 110 may be a two-photon microscope. Microscope 110 may be a benchtop or miniature microscope. Examples of suitable, commercially-available microscopes for use as microscope 110 include, but are not limited to, the Neurolabware (Los Angeles, Calif.) Resonant Scanning Two-Photon Microscope, the Intelligent Imaging Inovations (Denver, Colo.) Vivo 2-Photon System, and systems available from Bruker (Billerica, Mass.), Olympus (Waltham, Mass.), Thorlabs (Sterling, Va.), Scientifica (East Sussex, UK), Zeiss (Thornwood, N.Y.), or Leica Microsystems (Buffalo Grove, Ill.), etc. The adapter may also be used with custom-built two-photon microscopes, confocal laser scanning microscopes, etc.

In some embodiments, imaging of the target region 103 may be performed using light that is reflected, scattered, transmitted, or emitted by the sample or tissue within target region 103. In some instances, the light may emanate from the target region itself. Alternatively or in addition, light may be transmitted to the target region through the probe 102. The light provided through the optical probe may be at a near UV wavelength, visible wavelength, infrared wavelength, or any wavelength that may stimulate fluorescence at the target region. The light may be provided from an ambient environment, or a light source on-board, e.g., a two-photon microscope 110, another microscope 112 such as a one-photon microscope, and/or the adapter 100 itself. The light source may optionally be an LED light source. The light source may optionally be a laser. In some instances, the light may optionally be coupled with the adapter or microscopes by means of an optical fiber. Light delivered to the target region by the probe may be reflected or scattered from the target region and transmitted back through a GRIN lens of probe 102. Alternatively, the light collected from the target region and transmitted back through a GRIN lens of probe 102 may be light, e.g. one-photon fluorescence, two-photon fluorescence, or second harmonic light, that has been excited within the target region by the light transmitted to the target region by probe 102.

In one example, a microscope 112 may be directly coupled to an optical probe 102. The microscope may be mounted to the probe and/or a mounting structure, e.g., a baseplate. The microscope 112 may be a miniature microscope that is capable of being carried by the subject while the subject is freely moving. The microscope may be used to image the target region without use of the adapter. The microscope may then be removed from the probe, and the adapter may be attached to the probe. The microscope 112 may be attached to the adapter. In some instances, the adapter may be configured to fully or partially support microscope 112. Attachment of microscope 112 to the adapter may permit the microscope 112 to still be used for imaging the target region of a subject (while immobilized or freely moving), while also allowing another microscope 110 to image the target region (typically, after immobilizing the subject relative to the position of microscope 110). Such images may be viewed in parallel at the same time, or may be viewed sequentially. In some instances, an adapter may be used initially for imaging. The adapter may then be removed and then the microscope 112 may be directly attached to the probe. Different adapters may be swapped out. The different adapters may have different mechanical and/or optical properties, such as different objective lens focal lengths, numerical apertures, and/or mirror reflectance properties. The adapter may be an attachment that provides additional flexibility to the imaging system. In some instances, the adapter may be small and/or light weight enough that it is fully or partially supported by microscope 110. In some instances, the adapter may function as the objective for microscope 110, and may be used to image a live subject that has been immobilized relative to the position of microscope 110. In some instances, the adapter(s) may couple one microscope 110 to one or more microscopes 112 with different optical imaging properties. In some instances, the adapter(s) may couple one microscope 110 to two or more microscopes 112 with different optical imaging properties. For example, the adapter and/or mirror within the adapter may be used to direct light to multiple microscopes (e.g., miniature microscopes) with different optical filter sets. Optionally, the adapter(s) may couple one microscope 110 to three, four, five, six, seven, eight, nine, ten or more microscopes 112 with different optical imaging properties. The different optical imaging properties for the different microscopes may comprise, e.g., different imaging fields-of-view, different imaging resolutions, different fluorescence excitation wavelengths or wavelength ranges, different fluorescence emission wavelengths or wavelength ranges, etc.

As noted above, in some instances, the adapter may comprise a focusing mechanism used to align the focal plane of microscope 110 and the one or more microscopes 112. In order to align the focal plane of the two (or more) microscopes, a test target is imaged using, for example, a two photon microscope (110) and then the focusing mechanism of the adapter is adjusted such that microscope 112 will focus on the same target. In other instances, the focusing mechanism of microscope 112 is used to focus on the test target. The disadvantage of the latter procedure is that the optical settings (e.g., magnification, FOV) of microscope 112 may change during focusing. This may make it harder to compare images, e.g., images of a freely behaving subject with two photon images collected for the same subject.

As described above, the microscope 112 may be sized and/or shaped to be carried by the subject. For instance, the microscope may be a miniature microscope that may be carried by a rodent, such as a mouse, while the rodent may move about. The adapter may or may not be sized and/or shaped to be carried by the subject. For instance, the adapter may be a miniature component that may be carried by a rodent, such as a mouse, while the rodent moves about. The adapter may have any dimensions described for the microscope. The adapter may be larger than, smaller than, or have substantially equal size to the microscope. Alternatively, the adapter need not be so portable. The adapter may optionally be used when the sample or subject, or a target region of the sample or subject, is substantially immobilized.

In some instances, the adapter may be used connect two or more microscopes of the same or different type to a single optical probe, thereby enabling multimode imaging of a sample or subject. For example, microscope 112 may be a miniature epifluorescence microscope and microscope 110 may be a conventional bright field microscope, thus permitting simultaneous imaging of the sample or subject with accurate alignment of the two images. As another example, microscope 112 may be an miniature optogenetic microscope (e.g., a microscope comprising at least two light sources for imaging and photostimulation), while microscope 110 may be a one-photon or two-photon fluorescence microscope operating at a different fluorescence emission wavelength, thereby allowing simultaneous imaging of neuron activation and fluorescently-tagged biomarker distribution within a common field of view. In instances where microscope 112 is a miniature optogenetic microscope, the adapter may further comprise a compensator, as described above and depicted in FIG. 3 (e.g., a fixed compensator or a multi-position mirror holder that comprises a dichroic reflector in a first position and a compensator in a second position), to compensate for beam shift and improve the positional accuracy of the optical stimulation of single cells or other targets within the field-of-view.

In some instances, the adapter thus facilitates, for example, the correlation of image data collected for freely-behaving subjects (using microscope 112) and with structural, subcellular resolution image data collected using a two-photon (microscope 110). That is, the adapter facilitates comparison of images collected on two different length scales (cellular and subcellular).

In some instances, microscope 112 may be a fluorescence microscope, e.g., a miniature epifluorescence microscope), and microscope 110 may be a two-photon laser scanning microscope, or component thereof, used to provide photostimulation of optogenetically-modified neuronal tissue. In some instances, just the excitation light source for the two-photon microscope, e.g., a laser, may be used in conjunction with the adapter and microscope 110. In some instances, a laser light source or two-photon laser scanning microscope connected to interface 114 of the adapter may be used to provide a train of temporally focused laser pulses, for which axial beam profile may be controlled independently of lateral intensity distribution, to allow fast and selective excitation of individual optogenetically-modified neurons, or sub-cellular compartments thereof. In those instances where microscope 110 is a two-photon laser scanning microscope, or component thereof (e.g., a laser light source), the adapter may further comprise a compensator, as described above and depicted in FIG. 3 (e.g., a fixed compensator or a multi-position mirror holder that comprises a dichroic reflector in a first position and a compensator in a second position), to compensate for beam shift and improve the positional accuracy of the optical stimulation of single cells or other targets within the field-of-view.

In some instances, microscope 112 may be a bright-field or fluorescence microscope used for imaging a sample, e.g., a tissue sample, while microscope 110 may be a one-photon or two-photon microscope, e.g., a microscope comprising a scanning laser or patterned excitation light system, used to trigger a light-activated, CRISPR-based transcription system (e.g., the light-activated CRISPR-Cas9 approaches recently described by Nihongaki, et al. (2015), "Photoactivatable CRISPR-Cas9 for Optogenetic Genome Editing", Nature Biotechnology 33, 755-760; and Polstein and Gersbach (2015), "A Light-Inducible CRISPR-Cas9 System for Control of Endogenous Gene Activation", Nature Chemical Biology 11:198-200) for performing light-controlled genome editing in precisely defined subsets of cells, e.g., neurons, in a tissue sample. For example, in some instances microscope 110 may be used to trigger a light-activated, CRISPR-based transcription system for inserting, activating, and/or expressing nucleic acid sequences coding for channelrhodopsins (or other light-activated ion channels and ion pumps) and/or genetically-encoded calcium indicators (e.g., GCamPs) in selected neurons within a field of view, and microscope 112 may be configured to provide both photostimulation light for activating channelrhodopsin, thereby exciting the selected neurons, and imaging light for exciting GCamP fluorescence, thereby enabling imaging of neuronal signaling. In some instances, microscope 110 may be a one-photon or two-photon microscope used to trigger a light-activated Cre recombinase transcription system (Edwards, et al. (2009), "Light-Activated Cre Recombinase as a Tool for the Spatial and Temporal Control of Gene Function in Mammalian Cells", ACS Chem. Biol. 4(6):441-5). In these instances, the adapter may further comprise a compensator, as described above and depicted in FIG. 3 (e.g., a fixed compensator or a multi-position mirror holder that comprises a dichroic reflector in a first position and a compensator in a second position), to compensate for beam shift and improve the positional accuracy of the optical stimulation of single cells or other targets within the field-of-view.

In some instances, the accuracy of alignment/registration of images collected or video data recorded using microscopes 110 and 112, which are optically and/or mechanically coupled using the disclosed adapter may be further enhanced using an appropriate image alignment/registration algorithm to process the data following image acquisition. Images and/or video data may be captured or recorded using any of a variety of digital cameras (e.g., CCD cameras, CMOS cameras, etc.) that are attached to or incorporated into microscopes 110 and 112, and image acquisition and processing software (e.g., ImageJ (National Institutes of Health, Bethesda, Md.), Cell Profiler (the Broad Institute, Cambridge, Mass.), Icy (Institut Pasteur, Paris, France), LabVIEW (National Instruments, Austin, Tex.), MatLab (Mathworks, Natick, Mass.), etc.) known to those of skill in the art. A typical image acquisition workflow for use with the disclosed adapter and microscope imaging systems is illustrated in Example 1 below. A typical image registration workflow for use with the disclosed adapter and microscope imaging systems is illustrated in Example 2 below.

In some instances, operational parameters such as the adjustment of focus for microscopes 110 and/or 112 are performed manually prior to the start of image acquisition. In some instances, the setting of operational parameters such as focus adjustment may be facilitated through the use of real-time (i.e., "live") image acquisition and processing. For example, one application of the disclosed adapter is to compare image and/or video data captured for head-fixed and freely-behaving test subjects, e.g., laboratory animals. To facilitate the ability to focus on specific features and landmarks within the field-of-view during one-photon imaging, a real-time bandpass filter may be implemented that removes background signal and high frequency noise, and stretches the image contrast to facilitate focusing. Note that one-photon images are typically dominated by a bright background which impedes efficient focusing by visual feedback. The real-time image processing functionality (i.e., "live" bandpass filtering of a series of one-photon images) makes it easier to find specific features and landmarks in the specimen that is being imaged. Especially in low brightness images, the use of live filtering can help resolve landmarks and features that are otherwise indistinguishable from the background.

Figure 4:
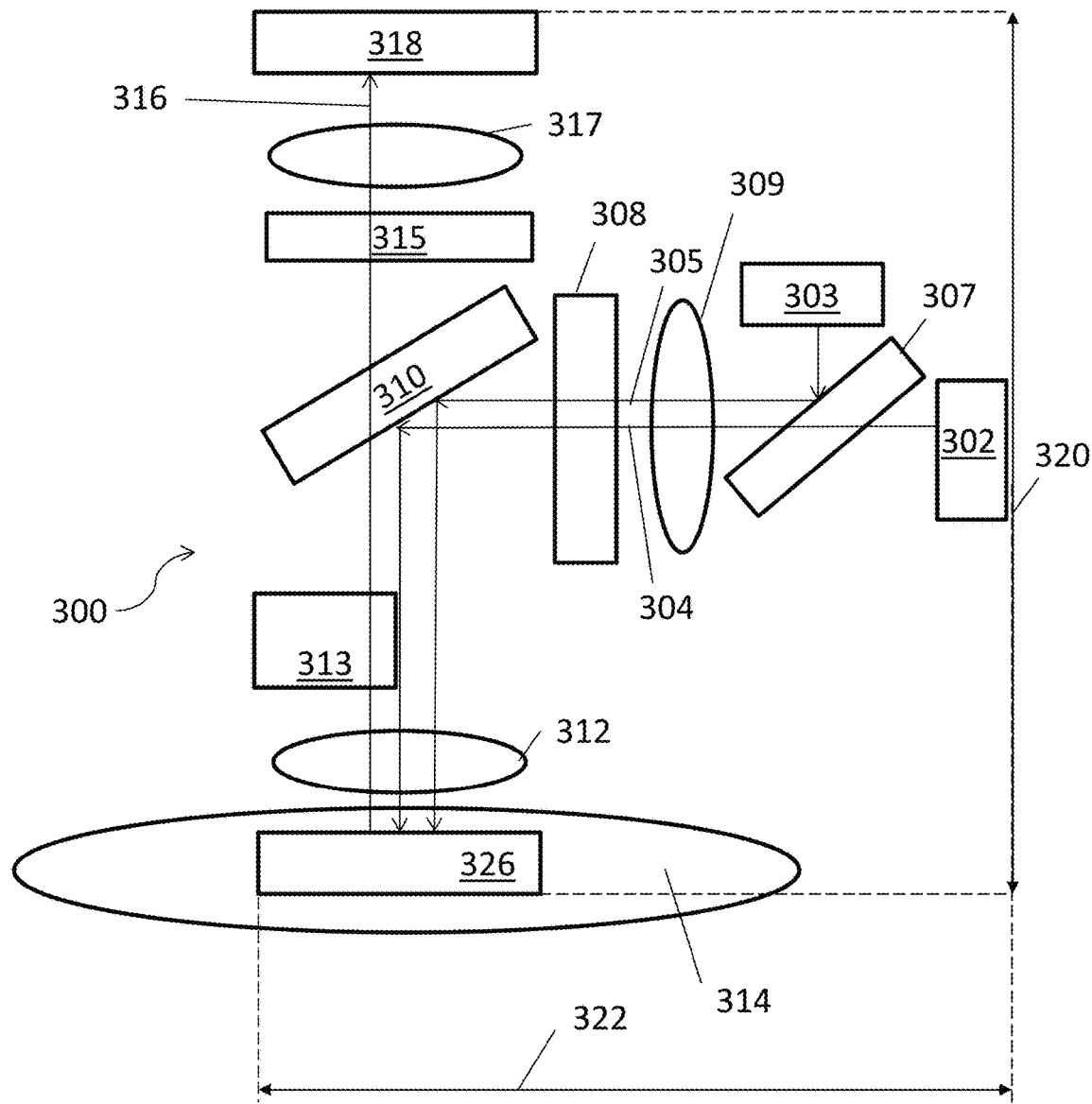
FIG. 4 shows a schematic diagram of an exemplary microscope that may be coupled to the adapter.

FIG. 4 illustrates a microscope that may be coupled to the adapter discussed herein. The microscope system 300 can include a plurality of optical elements (e.g., lenses, filters, mirrors, dichroics, etc.) within the dimensions 320 and 322 for the imaging of a target object 314. The optical elements can include a first optical arrangement 302 (e.g., light sources, diodes, fiber optics) that can generate a first excitation light 304, a second optical arrangement 303 (e.g., light sources, diodes, fiber optics) that can generate a second excitation light 305, a light source combining element 307 (e.g., dichroic filter), a condenser lens 309, an excitation filter 308 (e.g., short pass filter, band pass filter), an objective lens 312, (dichroic beam splitter) mirror 310, a tube lens 315, and an emission filter 317. While the microscope system is shown comprising a first and second optical arrangement, it is to be understand that one, or a plurality (e.g., three or more) of optical arrangements may be included in the microscope system.

The excitation light may induce an emission light 316 from the target object. A light 316 from the target object 314 can be directed from/by the objective lens 312 to an image capture circuit 318. The microscope system 300 may be configured to direct light from and capture image data for a field of view 326. The microscope system can additionally comprise one or more optical elements (e.g., filters) 313 configured to prevent or reduce chromatic aberrations. In some embodiments, the microscope system 300 can be configured to support wireless communication (e.g., via a wireless adapter). The wireless communication can be via a radio frequency or optical link. For example, one or more images captured by the microscope can be wirelessly communicated to an external processor communicatively coupled to a memory with instructions to receive the one or more images.

Not shown is a further dimension, which extends perpendicular to the plane containing dimensions 320 and 322. Although not necessarily limited thereto, each of these dimensions can be less than an inch. In some cases, dimension 320 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches. In some cases, dimension 322 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches. In some cases the dimension extending perpendicular to the dimensions 320 and 322 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches.

The microscope may comprise a housing. The housing may comprise the dimensions 320 and 322. The various elements illustrated in FIG. 4 may be integrated within the housing. The housing may partially or completely enclose the various elements. Optionally, some of the elements may be configured to be coupled to, but external to the housing. For example, light sources, or components of the image capture circuit may be external to the housing. Alternatively, the light sources, or components of the image capture circuit can be partially enclosed by the housing. Optionally, one or more elements can form part of the outer surface of the housing. Components such as the light sources or image capture circuits (e.g. printed circuit board including image sensors) that include electrical parts may be especially susceptible to damage by live beings or external forces.

Figure 5:
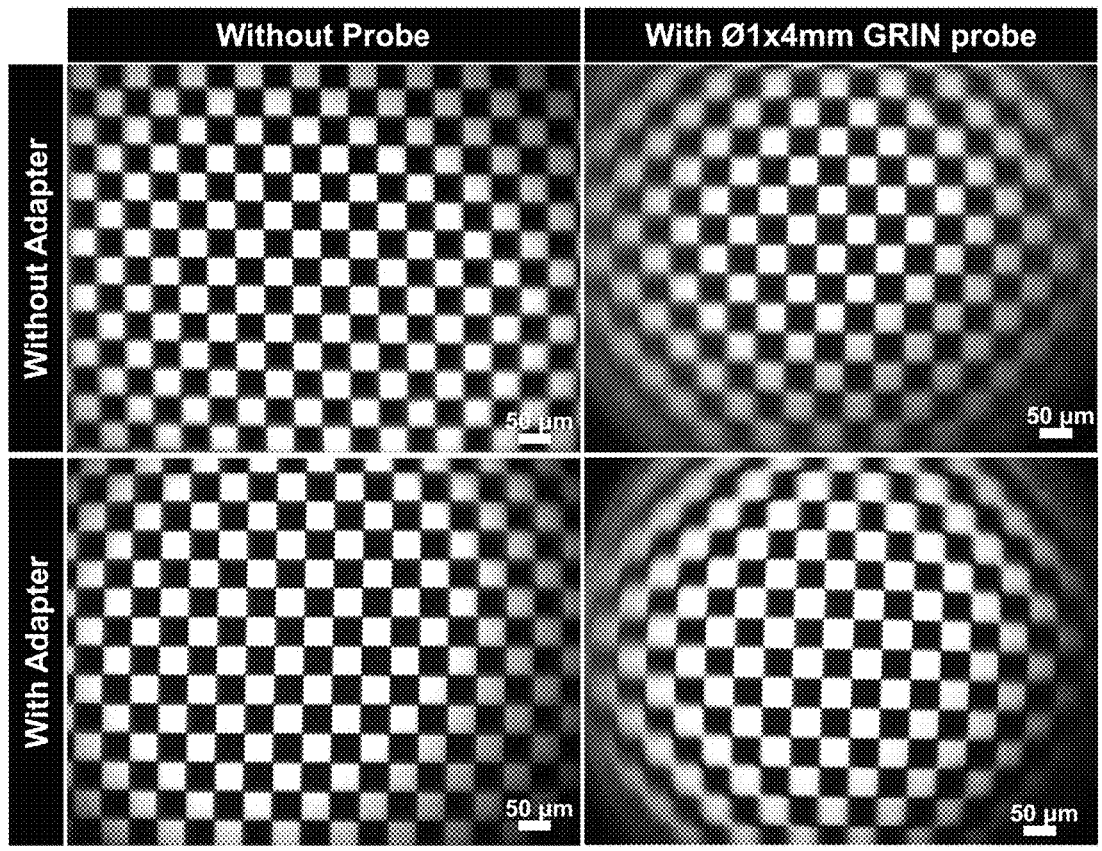
FIG. 5 shows examples of images of a 50 µm pitch test target captured using a miniature microscope with or without use of a 1 mm diameter GRIN probe, and with or without use of the disclosed adapter.

FIG. 5 provides examples of images collected using of images of a 50 μm pitch test target captured using a miniature microscope with or without use of a 1 mm diameter GRIN probe, and with or without use of the disclosed adapter. As can be seen, inclusion of the adapter in the optical path had little or no deleterious effect on the quality of the images captured by the miniature microscope.

Figure 6:
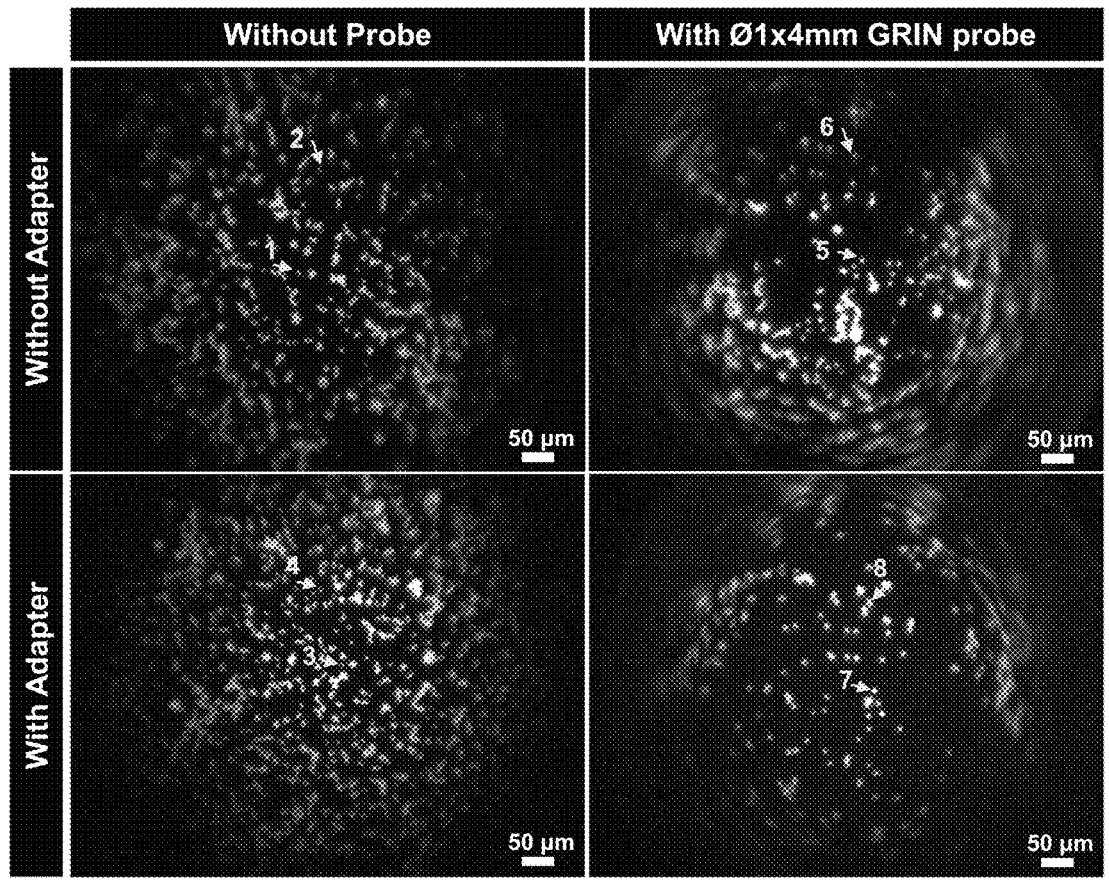
FIG. 6 shows examples of images of 7 µm diameter Dragon Green fluorescent beads captured using a miniature microscope with or without use of a 1 mm diameter GRIN probe, and with or without use of the disclosed adapter.

FIG. 6 provides examples of images of 7 μm diameter Dragon Green fluorescent beads captured using a miniature microscope with or without use of a 1 mm diameter GRIN probe, and with or without use of the disclosed adapter. As can be seen, inclusion of the adapter in the optical path had little or no deleterious effect on the quality of the images captured by the miniature microscope.

Figure 7:
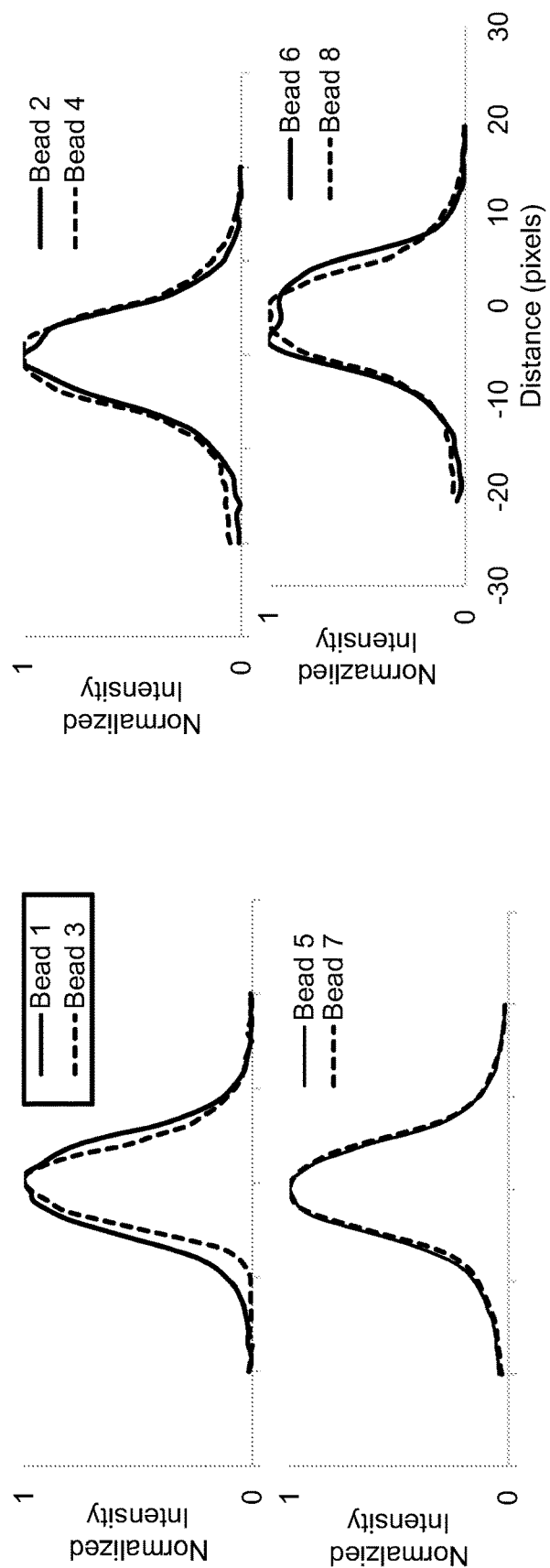
FIG. 7 shows examples of normalized fluorescence intensity plots of the beads indicated in each of the images in FIG. 6.

FIG. 7 shows examples of normalized fluorescence intensity plots of the beads indicated in each of the images in FIG. 6. As can be seen, the normalized intensity profiles for beads imaged with or without the use of the adapter are nearly identical, indicating that there is essentially no image distortion introduced by inclusion of the adapter in the optical path.

Example 1—Image Acquisition Workflow

This example illustrates one non-limiting approach to the use of the disclosed adapter for collecting one-photon and two-photon images:

1. Place a flat field test target under the adapter. For example, fluorescent beads (~7 μm in diameter) dried onto a microscope slide or onto the end of a straight GRIN probe may be used as a flat field test target.
2. Focus the two-photon microscope while the dichroic mirror on the adapter is positioned out of the light path.
3. Insert the dichroic mirror into the light path.
4. Focus on the test target using the one-photon microscope using the focusing wheel. The two microscopes are now focused on the same plane. If imaging though a GRIN lens inserted into the tissue, we recommend placing a GRIN lens with the same optical specifications on the test target and aligning the focal planes while imaging though the GRIN lens. This will more accurately compensate for optical aberrations in the GRIN lens.
5. Remove the test target and place the animal (or other samples) under the adapter.
6. Switch to the one-photon microscope and focus on the cell plane of interest.
7. Record one-photon video data (or capture still images) as needed, depending on the experimental goals.
8. Switch to the two-photon microscope and collect a z stack of images (i.e., a series of images wherein the focal plane of each subsequent image is displaced along the z- or optical axis) that contains the same target volume imaged with the one-photon microscope. We recommend collecting images over a z-axis range encompassing at least 50 um above and below the focal plane of the 1P microscope. This will ensure that the one-photon data captured or recorded falls within the sample volume encompassed by the collected z-stack images. In some instances, one may also collect dynamic volumetric recordings (e.g., recordings of cell firing from multiple cell planes that can then be registered with cells that fired during one-photon imaging. This may make the image contrast obtained for the one-photon and two-photon images more similar, and may enhance the image registration process).

9. Depending on the goals of the experiment, one can image using different indicators that fluoresce at different wavelengths (colors), and which may indicate either static or dynamic processes, or some combination thereof.

Example 2—Image Registration Workflow

One application of the disclosed adapter is for image registration and alignment of the images and/or video data captured or recorded simultaneously (or quasi-simultaneously) from the same sample or subject, e.g., a laboratory animal, using both two-photon and one-photon microscopes. This example illustrates one non-limiting approach used to register the two images:

1. Project the one-photon recording collected over time (i.e., a series of images or video data) into a single image (e.g., by projecting the maximum intensity image data on a pixel-by-pixel basis). We recommend projecting the maximum intensities to ensure that all of the cells that have fired during the recording have been included. The goal is to obtain a single image that shows all of the cells that have fired. Any image correction that may be required, e.g., motion correction, should be performed as necessary prior to the projection step.
2. Bandpass filter the projected image. This will remove the low frequency background and high frequency noise, and enhance the contrast for image registration. We currently use two methods for filtering:
    2a. Gaussian blur. A Gaussian blur of the image (also known as Gaussian smoothing) is subtracted from the original image to remove background, and a second Gaussian blur step is performed to remove high frequency content.
    2b. Gaussian filtering in Fourier space. This approach filters out large "structures" in the image (e.g., performs flat field or shading correction) and small "structures" (e.g., smooths the image) by removing large and small structures of the specified size using Gaussian filtering in Fourier space.
3. Identify the subset of two-photon z-stack images that correspond to the focal depth of the one-photon microscope. The focal depth of the one-photon microscope is much thicker than that for the individual two-photon optical image slices (e.g., the nVista miniature microscope currently has a depth of field of 20 µm, which is an order of magnitude thicker than a typical two-photon image slice). Therefore, the cells visible in the one-photon microscope image recordings may come from multiple planes. A non-limiting example of a method/algorithm for identifying two-photon optical sections that correspond to the one-photon focal depth is as follows:
    3a. Assume an initial guess for the number of two-photon optical slices corresponding to the focal depth of the one-photon microscope. For example, if the one-photon microscope has focal depth of 20 µm, and you have collected z-stacked two-photon images with a z-axis displacement of 3 µm per step (i.e., the optical slices are approximately 3 µm in thickness), the focal depth of the one-photon microscope corresponds to roughly 7 two-photon optical slices.
    3b. Generate a moving projection of two-photon optical slices. For example, project optical slices 1 to 7 into one image, slices 2 to 8 into a next image, slices 3 to 9 into a third image, and so on.
    3c. Bandpass filter the projections using the same filter as used in step 2.
    3d. Calculate the cross-correlation of the one-photon filtered image from step 2 with every image obtained in step 3c to identify the corresponding two-photon image.
4. To align/register the one-photon image and two-photon images identified in step 3d, we use an elastic registration algorithm. The main reason behind using an elastic registration algorithm is that spherical aberrations in the one-photon microscope are spatially different than those in the two-photon microscope. Therefore, the two images need to be aligned using translation, rotation, shear, and elastic deformations. The alignment/registration algorithm that is currently being used is based on vector-spline regularization, as explained in detail in Sorzano, et al. (2005), IEEE Transactions on Biomedical Engineering 52:652-663. Other alignment/registration algorithms have not been tested, but may also be used for this application (see, for example, Maes, et al., IEEE Transactions on Medical Imaging, Vol. 16(2), April 1997). The registration algorithm used primarily relies on minimizing contrast error between the two images. In addition, one can choose a set of one or more landmarks that appear in both images to help facilitate convergence of the algorithm to a single set of coordinate transformations. To obtain higher contrast for cells in the two images, e.g., when registration of dynamic GCaMP activity is desired, we recommend using volumetric imaging of the GCaMP activity. In this approach a time series recording is acquired in each optical slice (volumetric dynamic imaging), therefore, one needs to project recordings both in time and space (z direction). Cell firing will be recorded from multiple cell planes, and then registered with cells that fired during one-photon imaging. This will ensure that the image contrast for the two-photon and one-photon images is comparable, and will facilitate image registration.
5. Record the transformation (mapping) function calculated in step 4 and apply to the non-reference image to align the one-photon and two-photon images. Either image may be used as the reference image however, using the two-photon image as reference may facilitate image registration and further alignment.
6. Apply the mapping function to other corresponding images, e.g., if other channels/fluorophores have been recorded.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An adapter configured to optically couple to a plurality of microscopes, said adapter comprising:
   a) a first microscope interface configured to optically couple a first microscope to an optical element in optical communication with an optical probe;
   b) a second microscope interface configured to optically couple a second microscope to the optical element in optical communication with the optical probe; and
   c) an optical arrangement configured to direct light collected from a sample with aid of the optical probe to (1) the first microscope and second microscope simultaneously, or (2) the first microscope or second microscope selectively,
   wherein the first microscope interface and the second microscope interface are arranged relative to one another such that the first microscope and the second microscope have non-parallel axes.

2. The adapter of claim 1, wherein the first microscope is a one-photon microscope.

3. The adapter of claim 1, wherein the second microscope is a two-photon microscope.

4. The adapter of claim 1, wherein the first microscope and the second microscope are of different types.

5. The adapter of claim 1, wherein the first microscope and the second microscope have perpendicular axes.

6. The adapter of claim 1, wherein the first microscope interface is configured to permit the adapter to bear the entirety of the weight of the first microscope when the first microscope is attached to the first microscope interface.

7. The adapter of claim 6, wherein the first microscope weighs 20 grams or less.

8. The adapter of claim 6, wherein the first microscope has a volume of 30 $cm^3$ or less.

9. The adapter of claim 1, wherein the second microscope interface is configured to permit the second microscope to contact a housing of the adapter.

10. The adapter of claim 1, wherein the second microscope interface is configured to permit the second microscope to bear the weight of the adapter.

11. The adapter of claim 9, wherein at least a portion of the optical probe extends out of the housing.

12. The adapter of claim 9, wherein the optical element is contained within the housing.

13. The adapter of claim 1, wherein the optical probe comprises a GRIN lens.

14. The adapter of claim 1, wherein the optical element in optical communication with the optical probe is a mirror.

15. The adapter of claim 14, wherein the mirror is configured to rotate about an axis when the optical arrangement is configured to direct the light to the first microscope or second microscope selectively.

16. The adapter of claim 14, wherein the mirror is configured to translate linearly when the optical arrangement is configured to direct light to the first microscope or second microscope.

17. The adapter of claim 1, wherein the optical element is a beamsplitter or dichroic mirror when the optical arrangement is configured to direct the light to the first microscope and the second microscope simultaneously.

18. The adapter of claim 1, wherein the first microscope and the second microscope are configured to generate images based on the light collected from the sample.

19. The adapter of claim 18, wherein the adapter is configured to cause an image generated by the first microscope and an image generated by the second microscope to align.

20. The adapter of claim 1, wherein the first microscope interface and the second microscope interface allow the adapter to be coupled and decoupled from the first microscope and the second microscope.

21. The adapter of claim 1, wherein the second microscope interface is configured to allow the adapter to be coupled to a plurality of different types of microscopes.

22. The adapter of claim 21, wherein the second microscope interface and an adapter interface comprise threaded features that mate with each other.

23. The adapter of claim 1, wherein the first microscope interface is configured to be directly connected to an objective lens of the first microscope.

24. The adapter of claim 1, wherein the second microscope interface is configured to be directly connected to an objective lens of the second microscope.

25. The adapter of claim 1, further comprising a compensator to correct for beam shift and improve a positional accuracy of a stimulation light beam as it impinges on a target region within a field-of-view of the first microscope or the second microscope.

26. The adapter of claim 25, wherein the compensator is a fixed component of the adapter and is oriented at a 45° angle relative to the axis of the stimulation light beam.

27. The adapter of claim 25, wherein the compensator is installed in one position of a multi-position mirror holder which further comprises a dichroic reflector in a different position.

28. The adapter of claim 27, wherein the multi-position mirror holder is a rotary mirror wheel or a linear slider.

29. The adapter of claim 1, further comprising a housing wherein the first microscope interface and the second microscope interface are located on non-parallel surfaces of the housing.

30. The adapter of claim 29, wherein the housing has a maximum dimension of 20 cm.

31. The adapter of claim 29, wherein the collective weight of the housing and the optical arrangement is less than or equal to about 0.5 kg.

32. The adapter of claim 1, wherein the optical probe is attachable and separable from the adapter such that the adapter bears weight of the optical probe when the optical probe is attached.

33. The adapter of claim 1, wherein the first microscope is a one-photon microscope and the second microscope is a two-photon microscope, and wherein the adapter causes an image generated by the first microscope and an image generated by the second microscope that is different from the image generated by the first microscope to align.

34. The adapter of claim 33, wherein the image generated by the first microscope and the image generated by the second microscope are simultaneously displayed and overlapping.

35. A method for selectively exciting optogenetically-modified neurons in a tissue sample, the method comprising:
   a) providing the adapter of claim 1, wherein the first microscope is a one-photon microscope, the second microscope is a two-photon microscope, and the optical probe is in optical communication with the tissue sample; and b) using the two-photon microscope to deliver a train of temporally focused laser pulses to selectively excite individual optogenetically-modified neurons, or subcellular compartments thereof.

36. The method of claim 35, wherein the first microscope is a one-photon epifluorescence microscope.

37. The method of claim 35, wherein the first microscope is a miniature microscope having a weight of 4 grams or less.

38. The method of claim 35, wherein the first microscope is a miniature microscope having a volume of 500 mm$^3$ or less.

39. The method of claim 35, further comprising the use of real-time bandpass filtering of a series of images captured by the one-photon microscope to facilitate focusing.

40. A method for enhancing the accuracy of alignment of images captured by a one-photon microscope and a two-photon microscope, the method comprising:
   a) providing the adapter of claim 1, wherein the first microscope is a one-photon microscope, and the second microscope is a two-photon microscope;
   b) projecting a series of images captured by the one-photon microscope into a single image;
   c) applying a bandpass filter to the projected image created in step (b) to remove low frequency background and high frequency noise;
   d) identifying a subset of images selected from a z-stack of two-photon optical image slices that overlap with a focal depth of the one-photon image by:
      (i) generating a moving projection of two-photon optical image slices, wherein the number of two-photon optical image slices included in the projection is determined by dividing the focal depth of the one-photon image by a thickness of a two-photon optical image slice, and wherein the starting optical image slice for a subset of the two-photon optical slices included in the moving projection is incremented by a value of one for each sequential projection;
      (ii) applying the same bandpass filter as used in step (c) to each of the two-photon projections created in step (d)(i); and
      (iii) calculating a cross-correlation between the filtered one-photon image of step (c) with each of the filtered two-photon projection images of step (d)(ii) to identify that which is best correlated with the one-photon image;
   (e) applying an elastic registration algorithm to the filtered one-photon image of step (c) and the filtered two-photon projection image identified in step (d)(iii) to generate a set of coordinate transformations; and
   (f) applying the coordinate transformation to the filtered one-photon image of step (c) or the filtered two-photon projection image identified in step (d)(iii) to align the images.

41. The method of claim 40, further comprising the use of real-time bandpass filtering of a series of images captured by the one-photon microscope to facilitate focusing.

42. The method of claim 41, wherein the elastic registration algorithm is a vector-spline regularization algorithm.

* * * * *